US010004476B2

(12) United States Patent
Willems et al.

(10) Patent No.: US 10,004,476 B2
(45) Date of Patent: Jun. 26, 2018

(54) PORTABLE ULTRASOUND SYSTEM ALTERNATIVELY ATTACHABLE TO TABLE BASE AND FOREARM CONTACT PART

(71) Applicants: John Willems, Maastricht (NL); Joop Geijsen, Maastricht (NL)

(72) Inventors: John Willems, Maastricht (NL); Joop Geijsen, Maastricht (NL)

(73) Assignee: ESAOTE S.P.A., Genoa (IT)

( * ) Notice: Subject to any disclaimer, the term of this patent is extended or adjusted under 35 U.S.C. 154(b) by 0 days. days.

(21) Appl. No.: 14/658,573

(22) Filed: Mar. 16, 2015

(65) Prior Publication Data

US 2015/0182197 A1  Jul. 2, 2015

Related U.S. Application Data

(63) Continuation-in-part of application No. 13/003,742, filed as application No. PCT/EP2008/060187 on Aug. 1, 2008, now abandoned.

(51) Int. Cl.
A61B 8/00 (2006.01)
A61B 8/14 (2006.01)

(52) U.S. Cl.
CPC ............ *A61B 8/462* (2013.01); *A61B 8/4427* (2013.01); *A61B 8/14* (2013.01); *A61B 8/465* (2013.01)

(58) Field of Classification Search
CPC ......... A61B 8/14; A61B 8/4427; A61B 8/462; A61B 8/465
USPC ....................................................... 600/459
See application file for complete search history.

(56) References Cited

U.S. PATENT DOCUMENTS

| 5,293,300 | A | * | 3/1994 | Leung | G06F 1/1616 361/679.59 |
|---|---|---|---|---|---|
| 5,609,485 | A | * | 3/1997 | Bergman | G01S 7/52055 128/916 |
| 6,126,608 | A | * | 10/2000 | Kemme | A61B 8/00 600/459 |
| 6,258,028 | B1 | * | 7/2001 | Byeon | A22B 5/007 600/437 |
| 6,575,908 | B2 | * | 6/2003 | Barnes | A61B 5/0402 600/437 |
| 8,029,452 | B2 | * | 10/2011 | Kliewer | A61B 8/4281 128/845 |
| 2003/0060714 | A1 | * | 3/2003 | Henderson | A61B 8/00 600/459 |
| 2003/0078501 | A1 | * | 4/2003 | Barnes | A61B 5/0402 600/446 |
| 2004/0226973 | A1 | * | 11/2004 | Kao | F16M 11/041 224/218 |
| 2005/0251035 | A1 | * | 11/2005 | Wong | A61B 8/00 600/437 |

(Continued)

*Primary Examiner* — Amanda Lauritzen Moher
(74) *Attorney, Agent, or Firm* — Themis Law

(57) ABSTRACT

A portable ultrasonic diagnostic system includes a probe transmitting and receiving an ultrasonic signal to and from a region of interest, and a main unit having circuitry in communication with the probe to form an image based on the ultrasonic signal and a display displaying the formed image. The main unit has a weight which can be supported by one arm and is provided with a handle to be grasped by one hand. The main unit has a case in the form of a tablet computer, with a front side formed by a display and a rear side, and further has a handle.

24 Claims, 17 Drawing Sheets

(56) References Cited

U.S. PATENT DOCUMENTS

2007/0165026 A1* 7/2007 Engel .................. G06T 15/08
                                                    345/424
2008/0300489 A1* 12/2008 Schutz ................ A61B 5/6826
                                                    600/459

* cited by examiner

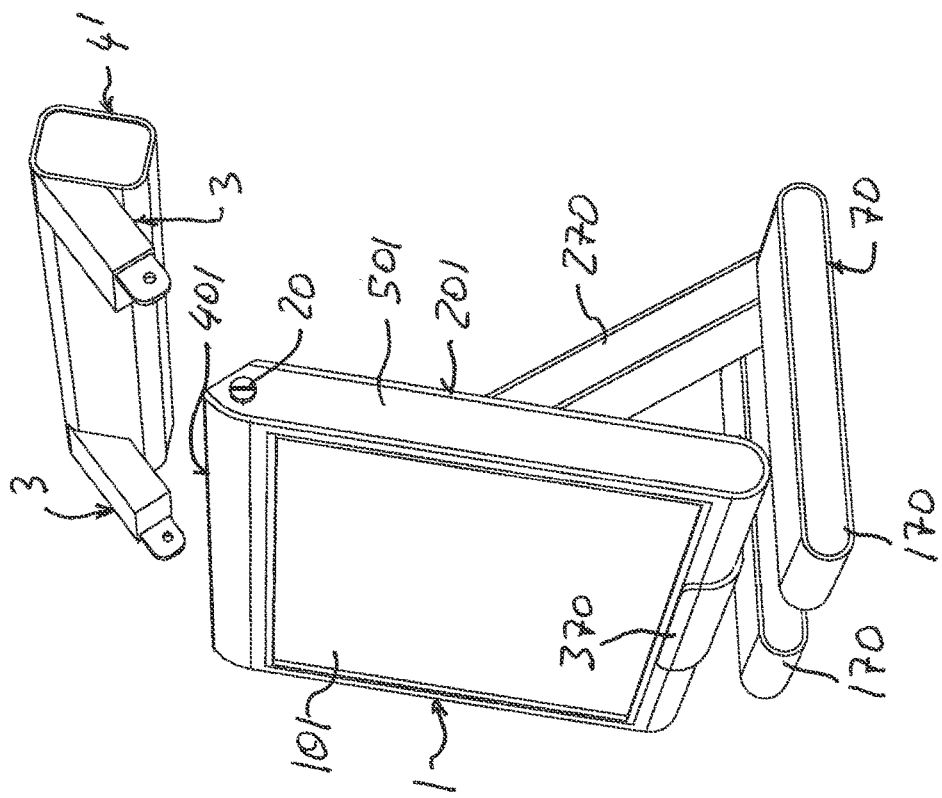
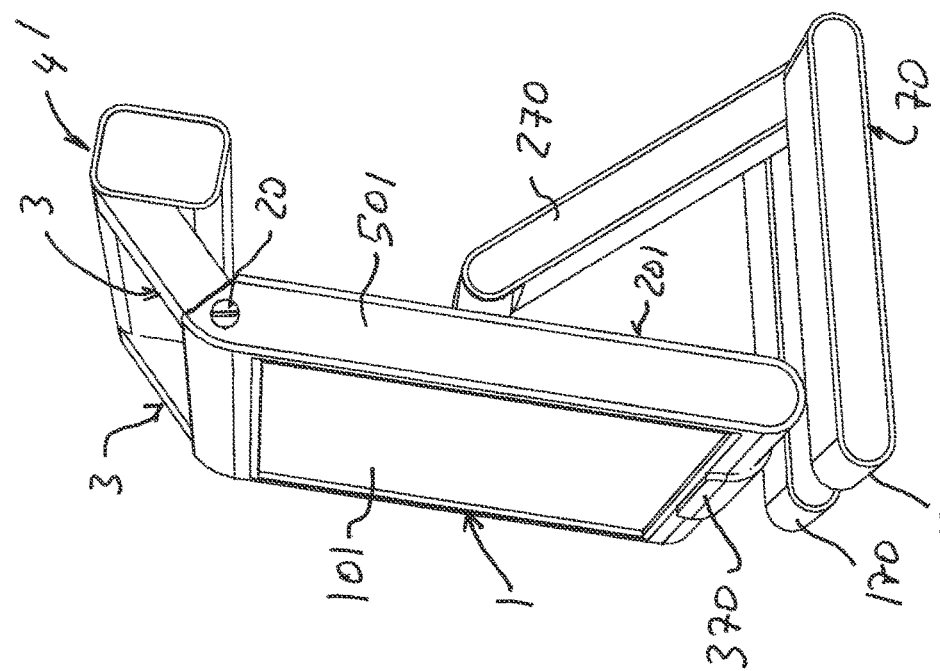

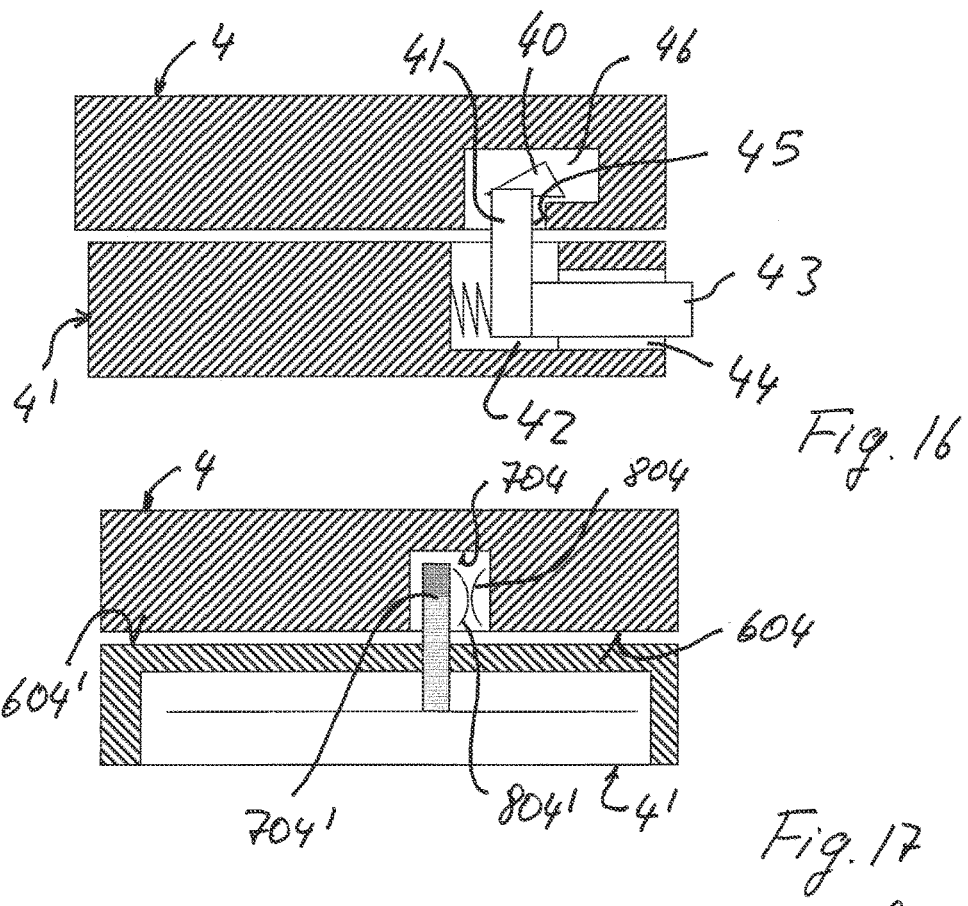
Fig. 16
Fig. 17
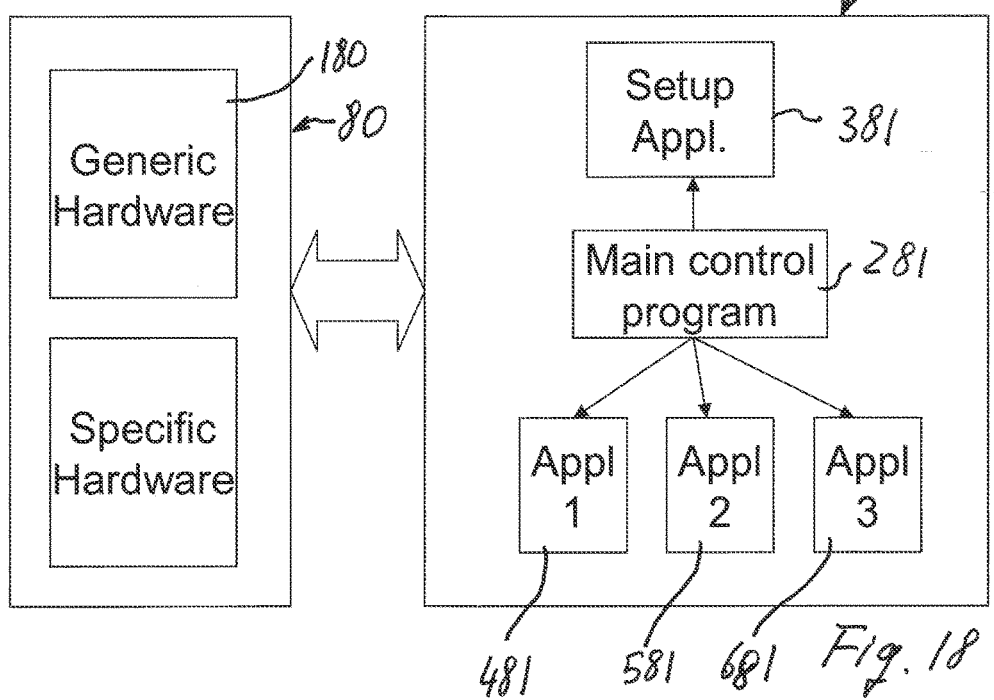
Fig. 18

PORTABLE ULTRASOUND SYSTEM ALTERNATIVELY ATTACHABLE TO TABLE BASE AND FOREARM CONTACT PART

FIELD OF THE INVENTION

The invention relates to portable ultrasonic diagnostic systems, and, in particular, to a portable ultrasound diagnostic system that includes:

a probe for transmitting and receiving an ultrasonic signal to and from a region of interest;

a main unit having circuitry in communication with the probe for forming an image of the region of interest based on the ultrasonic signal and;

a display for displaying the formed image;

the probe being connected to the said circuitry in the main unit by means of a cable connection;

the main unit having a weight which can be supported by one arm, and;

the main unit being provided with handle means to be grasped by one hand.

BACKGROUND OF THE INVENTION

Ultrasonic systems or devices of the diagnostic kind are known and are the result of advances in the underlying technology, which have permitted miniaturization of the necessary electronics. The ultrasound industry continues to reduce the size and weight of available diagnostic equipment. The smaller and lighter equipment has improved portability, however, existing portable ultrasound technology is not without its limitations.

One shortcoming of some portable systems is that the need to hold onto or otherwise manipulate the equipment with both hands during use hinders the ability of a person to productively use the system in some situations. For example, document U.S. Pat. No. 5,590,658 discloses an ultrasound system including a laptop computer with the capability of displaying ultrasound images obtained with a handheld scan head. With this kind of system, in order to ensure that the display is visible at all times during acquisition of the ultrasound signals with the scan head, the user must either hold the laptop computer, or change the position of the laptop computer to face the user, who may be moving around to position the scan head in a suitable location during the imaging session. As a result, the system user's hand that is not being used to manipulate the scan head is often nonetheless occupied and not always free to assist with the medical procedure.

The portable ultrasound systems, disclosed in U.S. Pat. Nos. 5,722,412 and 5,738,099, are of the kind that is so-called "hand held" and integrate the display and the transducer in the same unit. While in essence permitting the scan head and the display to be held in one hand, these systems suffer from a different shortcoming. In particular, in order for the ultrasound user to get the desired view, it is frequently necessary to move the transducer repeatedly to different regions of the patient and to different orientations. In so doing, the displays of these systems may not be sufficiently visible to a user unless that user moves about, possibly into awkward positions.

A further kind of portable ultrasound systems is disclosed in document U.S. Pat. No. 6,126,608. This kind of devices includes a scan head and a main unit. Circuitry forms the image based on the ultrasound signals collected by the scan head. A display screen is carried by the main unit and displays the ultrasound image. The main unit is relatively small and is provided in combination with an attachment member, which is mountable around a forearm of the system user such that said display is visible to the system user during use. The attachment member extends toward a hand of the system user at the end of the forearm and includes a digit-accommodating opening.

Although this ultrasound system overcomes the shortcomings of the above mentioned known systems, by leaving a hand free to carry out help functions during imaging while permitting at the same time to have the display always optimally directed against the user, so that the said user can have the best view of the display, there are still shortcomings which consist principally in that:

The display is very small in size, and

The hand at the arm, to which the main unit is attached, cannot carry out any tasks or functions connected to the device such as controlling the device by means of control buttons or the like. These tasks must be carried out by the hand carrying the probe so that in certain situations the scanning process must be interrupted or even aborted due to the fact that some controls has to be activated on the main unit.

A general drawback of the increasing miniaturisation trend of the ultrasound systems consists in that said portable systems are limited of certain specific applications of the ultrasound imaging technique and that, in order to have systems able to carry put different kinds of applications of the ultrasound imaging technique, bigger and less portable devices are still needed.

Thus, it would be desirable to provide a portable ultrasound system which overcomes these and other shortcomings of the prior art that were discussed above.

SUMMARY OF THE INVENTION

The present invention provides a portable ultrasound system, in which the main unit has a case in the form of a tablet computer, with a front side formed by a display, a rear side, and a handle. The handle is formed by an elongated member, which is secured to the case of the main unit by cantilevered arms protruding from the case in a direction of the rear side of the case of the main unit, terminating behind the rear side so that the elongated member forming the handle extends at a certain distance behind the rear side of the case of the main unit and is nearer to one of two opposite peripheral edges of the case of the main unit.

In a portable ultrasound system according to the invention, when one hand grasps the handle, the case of the main unit leans against the forearm, the weight of the main unit is carried by the forearm and the hand has only the function of blocking the case of the main unit in position.

The main unit case has the form of a flat parallelepiped. In particular, it has two larger sides which form the front and the back side and which are connected by smaller sides being the lateral sides.

The front side is formed substantially entirely by a so called touch screen, such that no key or button or other kind of control is provided on the sides of the case of the main unit. "Substantially" may mean that in different embodiments the touch screen may cover between 65 and 100% of the front face.

In one embodiment, the front and the back sides of the case of the main unit are rectangular.

The main unit comprises all of the hardware and peripherals of the ultrasound system needed for driving the ultrasound probe and for generating, processing and storing the images. Additional hardware is provided which is of general purpose such as communication units with other devices, networks or other external peripherals. The transducers are housed in a probe together with some electronic components as typical in current traditional ultrasound probes.

Advantageously, the elongated member forming the handle is provided at a distance from a peripheral edge of the case of the main unit, which is on the opposite side of the peripheral edge of the said case nearer to said elongated member, that distance being not longer than the average distance from the palm of a hand to the hollow of an elbow.

According to still another improvement, in order to adjust the distance of the elongated member from the peripheral edge on the side of the case opposite to the peripheral edge to which the elongated member is nearer, the arms supporting the elongated member are secured to the case of the main unit and/or to the ends of the elongated member in a swingable way, and particularly in a swingable way around an axis parallel to the axis of the elongated member.

According to another improvement, the elongated member is hollow and forms a case for housing at least part of the circuitry of the main unit. In particular, the elongated member forms the housing for a battery pack.

According to a first alternative, the elongated member is in the form of a case for housing interchangeable battery packs, an opening being provided in the elongated member which allows extracting the battery packs from or inserting it in the elongated member.

A second alternative provides that the elongated member forms an enclosure for the battery packs and the electric wires, and that the battery packs are fixedly mounted in the enclosure.

In both cases the elongated member is at least partly hollow and forms a chamber, which has an open side and a door for closing the open side. Furthermore, in the chamber there are provided electric contacts, which cooperate with the electric contacts of a battery pack having predetermined dimensions and a shape corresponding to the dimensions and to the shape of the chamber.

In this case, the electric cables for feeding the power to the circuitry inside the case of the main body pass inside one or both of the two lateral arms and from then inside the case of the main body.

An additional variant provides that the elongated member has several separated chambers, each shaped to hold at least one or a number of battery packs and limited relative to the total number of battery packs which can be housed in the elongated member. Each chamber has an opening for inserting and extracting the corresponding battery pack or battery packs and has also removable means for closing the opening, each of the chambers being provided with contact terminals of a power feeding line connected to the power input of the main unit by conductors passing through one or both of the arms linking the elongated member to the case of the main unit.

It has to be emphasized that the term battery pack, in the present description and in the claims, is meant to identify a rechargeable or non rechargeable battery formed by one piece or a group of pieces, which are electrically connected and integrated in a power unit having a certain number of singular pieces electrically connected such to have a certain voltage and a certain power and endurance.

According to still another variant, the elongated member has at least one chamber in which a power feeding circuit is housed, said circuit having means for connecting to an external power network or source and an output connected to the power feeding line of the main unit, which is provided in the elongated member.

Advantageously, a battery pack recharger is also provided, which is fed by the power circuit and which is connected to the battery packs in the elongated member by means of the power feeding line present in the elongated member or to a separate recharging line, which is provided in the elongated member and which branches in each one of the chambers housing the battery packs. The recharging line in the chambers has terminal contacts which are electrically connectable to the recharging inputs of each of the battery packs.

It has to be noted that, as done for example for notebook computers, the chamber housing a battery pack and the battery pack itself each have a part of an electric multipolar connector, which cooperates one with another for generating the electric connections between the inputs and outputs of the notebook and of the battery pack when the battery pack is inserted in the chamber.

According to another improvement, the elongated member carries at least one or more control buttons or keys, which are connected to the circuitry of the main unit for generating and sending commands to the main unit and activating or deactivating functions of the ultrasound system.

The elongated member forming the handle is oriented advantageously parallel to a peripheral edge of the display. This allows carrying the main unit easily in the correct orientation of the display for the user.

According to still another improvement, the case of the main unit can be carried easily either in a so called portrait or in a so called landscape orientation of the display, this means according to two orientations of the display which are rotated of 90° one with respect to the other around an axis of rotation that is perpendicular to the display and passes through the center of the display area.

When the display is rectangular in shape, the display is oriented with the longer edges along a horizontal direction (landscape orientation) in a first orientation and with the longer edges in a vertical direction (portrait orientation) in a second orientation.

In the said first orientation, the elongated member forming the handle of the case of the main unit is also horizontal, while in the said second orientation the elongated member is oriented to be contained in a vertical plane.

In order to have a secure support of the main unit case in both the first and second orientations, the length of the case of the main unit in the direction parallel to the longitudinal axis of the elongated member is less than twice the average distance from the palm of the hand to the hollow of the elbow.

This feature ensures that when the main unit is held in a position with the handle, i.e. the elongated member, in a vertical plane, the case is balanced and there is no major contribution of the weight in the part of the case protruding over the zone at which the hand grasps the elongated member.

In order to further facilitate the carrying of the main unit, reducing the stress or work of the hand to firmly block the case grasping the handle, and so enabling use of the hand for pressing the keys or buttons arranged on the elongated member, the invention provides, in one embodiment, for an ultrasound system with one or more of the features disclosed above and having also an attachment member for said main unit case, said attachment member being mountable around a forearm of the system user such that said display is visible to the system user during use.

In its simplest form, the attachment member is formed by at least one strap secured to the back side of the case of the main unit, i.e. the side oriented towards the forearm of the user. The strap has two ends which carry means for securing the two ends one to the other and for tightening the strap around the user forearm.

The straps are provided in an intermediate position between the elongated member and the side of the case of the main unit opposite to the one which is nearer to the elongated member.

Furthermore, the at least one strap can be secured to the back of the case of the main unit to be rotatable around an axis perpendicular to the back side of the case of the main unit, such that the main unit can be rotated in one of the first and second orientations of the display when the strap is tightly secured to the user's arm.

In another embodiment, the attachment member is formed by a combination of a strap and an anatomic saddle-like contact part against the forearm. In this case, the saddle like contact part is secured to the back of the case of the main unit in a rotatable way around an axis perpendicular to the back side of the case.

The system therefore further comprises an anatomic saddle-shaped contact part which is configured to be fitted onto the forearm and which is attachable to the main unit by means of snap fasteners and a table base which is attachable to the main unit by means of snap fasteners.

The main unit can be alternatively attached to the saddle-shaped contact part and to the table base, the said snap fasteners being the same for the saddle-shaped contact part and for the table base.

This can achieve a great versatility because the main unit can be supported by one arm or by a table base and the connecting means for the saddle-shaped contact part and for the table base are the same. This means that the configuration can be easily and quicky switched and the system can be produced without different dedicated connecting means for all the intended uses, but only a single type is provided.

The saddle-shaped contact part has a distance from the handle such that when the saddle-shaped contact part is secured to the forearm the hand can grasp the handle in such a way that fingers are free to move and operate on the handle.

Furthermore, means may be provided for releasable stopping the saddle like contact part in one angular position of the at least two angular positions corresponding to the above mentioned first and second orientations of the display.

This can be obtained by means of elastically releasable stopping means, which are mounted in housings provided in the back side of the case of the main unit or in the surface of the saddle like contact part adhering to the back side of the case. Those means have one or more teeth or projections that are forced in a position to protrude out of the surface of the back side and can be pushed back in a position not protruding for the back side. Those teeth or projections cooperate with notches provided in the surface of the saddle-like contact part adhering the back side and are placed on a circular path coaxial with the axis of rotation of the notches.

This is applicable also to the table base, so that the orientation of the main unit can be performed in the same way with the saddle-shape contact part and the table base.

The elongated member carries at least one or more control buttons or keys, which are connected to the circuitry of the main unit and generate and send commands to the main unit and activate or deactivate functions of the portable ultrasound system, said buttons or keys being actuatable by all the fingers of the hand.

This means that not only the thumb can act on the buttons, but all the fingers of the hand can freely operate on the buttons like a musical instrument.

This feature is allowed also by the fact that the handle comprises two flat and parallel longitudinal surfaces parallel to the main unit, which are larger than the transverse surfaces, which transverse surfaces connect the longitudinal surfaces and are therefore perpendicular to the main unit.

According to still another feature of the present invention, in order to be able to use the device for a longer time without any connections to an external power source, in combination with the case of the main unit additional power units can be provided consisting in a case for more battery packs. Said case and the case of the main unit have releasable mechanical connection means and releasable electric connection means between the power unit output line and the main unit power input line.

One embodiment provides for an additional elongated element as the handle, which can be mechanically secured to the handle and which is in the form of an enclosure where the battery packs are stably housed, or in the form of a case for housing battery packs such that they can be extracted from and inserted in the case for substitution with charged battery packs.

According with another embodiment, which can be provided in combination or separately from the previous one, the elongated member forming the handle is secured to the case of the main unit in a releasable way, while two or more different elongated members are provided which are different in size one from the other, and particularly which have different cross-sections such to house a different number of battery packs. The releasable attachment of the elongated members has the same shape and dimensions for every elongated member so that each of the different elongated members can be secured to the case of the main unit.

The means for releasably securing the elongated member to the case of the main unit can be of every kind and lies within the general knowledge of the skilled person. Particularly, these means can be releasable snapping means, screw-connections, or similar.

An additional feature can be provided separately or in combination with each of the features disclosed above, wherein the power unit can be part of a docking unit, which is formed by a case having the same form from a plan view as the case of the main unit and certain thickness.

The docking unit can be the housing not only for supplementary battery packs but also for additional peripherals such as: special computing circuitry, storage devices, reading/writing devices of portable storage media like floppy, CD-ROM, DVD-ROM or similar, modems or other communication hardware, ports for connection of peripherals, like USB, Firewire, parallel and/or serial ports, hardware and ports for the connection to a network, and other devices.

Similarly to the above mentioned elongated member of the handle, the case of the docking unit and the case of the main unit are provided with means for securing one to the other in a releasable way, mechanically and also electrically.

Even in this case, releasable snapping means can be provided or other particular means, which ensure a rapid attachment and a rapid separation of the case of the main unit to or away from the case of the docking unit in combination with connectors for the power feeding lines between the power sources in the docking unit and the circuitry in the main unit, and for the communication lines of the peripheral and other devices housed in the docking unit and listed above.

As a one more alternative, the additional battery packs and/or the additional hardware may be housed in the anatomic saddle like contact part which has been disclosed above. Also in this case, since the saddle contact part can be releasably secured to the back side of the case of the main unit, a set of different saddle like contact parts can be provided, which differ one from the other in their dimensions so to be able to house a different number of battery packs and/or one or more different additional hardware units.

The saddle like contact part can also be provided as unit formed by several parts which can be mounted one to the other when needed. In this case, for example, an additional case like element can be provided to be secured in an intermediate position between the saddle like contact part and the back side of the case of the main unit, while advantageously the additional case like element has, on one side to be connected to the backside of the case of the main unit, the same connection means as the side of the saddle like contact part, while on the side to be connected to the saddle like contact part it has the same connection means as the ones provided on the back side of the case of the main unit. This construction allows also providing more than one additional case like element, which can be secured one to the other and in an intermediate position between saddle like contact part and back side of the case of the main unit.

It has to be understood that the above features of the present invention can be provided alternatively or in any combination or subcombination one with the other depending on the configuration needed for the ultrasound diagnostic system.

Thanks to the above conditions, the portable device can be configured in such a way as to set a certain endurance of the power source, while carrying out certain tasks and limiting of the weight in view of the power source endurance and of the tasks which can be carried out.

Typically the endurance of the power source, i.e. the battery use is about four hours, while the weight is not lower than 5.5 kg.

In its lightest configuration, the weight is about 3 kg, but the endurance of the power source is limited to about one hour.

Since in portable ultrasound systems, the endurance of the electric power and the weight are important limitations in comparison to the conventional sonographers, an embodiment of the present invention has an additional feature which can be provided in any combination or subcombination with the above disclosed features and even separately. The ultrasound systems can be used for carrying out different imaging tasks in relation with diagnostic and/or surgical or mini-invasive surgical applications. While conventional echographic systems have the capacity of carrying out every or a great part of the above tasks, due to the limits disclosed above the portable device are also limited in relation to the different possible kinds of application they are able to carry out.

In the known portable ultrasound systems of the so called "hand-held" or "notebook" kind, in order to reduce power consumption, it is known to limit the feeding of power only to the electronic units which are needed for carrying out the tasks connected to certain specific applications which have been selected by the user. In any case the user interface is always completely active.

According to an additional feature of the present invention, the portable ultrasound system of the above kind has in the case of the main unit a completely graphical user interface. In this case the screen is a touch screen able to receive commands by touching the screen. The different control keys, buttons, switches and cursors are in the form of graphic symbols representing the keys, buttons, switches and cursors. Selecting means are provided for selecting at least one specific application within a list of applications which are available on the portable echographic system, means being provided for loading and executing a specific graphic user interface program which generates on the screen the images of only the keys, buttons, switches and cursors that are needed for carrying out the tasks related to the selected specific application.

Furthermore, according to an additional feature, in the portable echographic system different electronic units for carrying out specific tasks are substituted by a central processing unit configured to execute different programs and to carry out different tasks, at least a memory being provided in which there are saved different programs for controlling the central processing unit in and carry out different specific tasks related to the functions of an echographic system. One or more of the different programs for carrying out specific tasks are loaded by the central processing unit and executed by it when a certain specific application has been selected by the user.

Advantageously, a main control program can be loaded and executed by the central processing unit, which prints on the display screen the list of applications available with the portable system and a graphics user interface comprising the icons of keys, buttons, switches, cursors or similar control devices related to general functions, such as a menu for addressing the specific diagnostic or surgical applications, menus for addressing configuration and adjustments options for the device which are of general purpose, and/or menus for carrying out maintenance or managing tasks of the apparatus and of the devices integrated in it such as file manager routines, memory drives control and maintenance routines, electronic units configuration and diagnostics, driver upgrades, system upgrades and additional typical tasks needed for managing and for maintaining the efficiency of a computer system.

In particular, as soon as the apparatus is started, all touch screen drivers and menu graphic interfaces are loaded and executed.

The main control program addresses, depending on the choice made with the help of the menus, the programs for carrying out the specific tasks related to the applications or configuration and adjustment options chosen by the user.

According to another advantageous feature of the present portable echographic system, one more program is saved in the memory and is available for being executed by the central processing unit. That program consists in an application specific tutorial for the user which is already provided in the echographic system in a ready to start condition.

In this case, the main control program prints on the screen a graphic user interface with a key icon, which addresses the tutorial program. The key, when touched by the user, causes the main control program to load the tutorial program and to have the program executed by the central processing unit.

A main tutorial control program can be executed, which loads a graphic user interface showing a list of options, each of which can be highlighted and chosen by means of the touch screen interface and which cause the corresponding specific program to be executed and the corresponding graphic user interface to be loaded and printed on the touch-screen display. In order to spare electric power and maintain a limited weight without affecting the computational power of the system needed by the hardware for executing the programs and carrying out the tasks of the system, according to another feature, in one embodiment a part of the tasks to be carried out by the central processing unit (CPU) are carried out by the graphic processing unit (GPU). In ultrasound devices the GPU is not subjected to high operational stresses because image processing is not a heavy operation. Computational power is normally needed to extract image data from the signals received. Thus, the GPU can be used as an aid to the CPU also for carrying out non typical tasks for the GPU. In the present embodiment, the portable ultrasound system has a scan converter which is formed by software to be executed by a processing unit while the graphic processing unit is used as the processing unit for executing the scan converter software.

Additional features of the present invention are disclosed in the dependent claims.

BRIEF DESCRIPTION OF THE DRAWINGS

The above features and the related advantages will become clearer form the following description of preferred embodiments which are illustrated in the annexed drawings.

FIGS. 14 and 15 illustrate the same views as FIGS. 12 and 13 but with an elongated member having a thicker cross section than the one of FIGS. 12 and 13.

FIG. 16 illustrates a detail of an example of releasable connection means which can be used for attaching the different add-ons disclosed in the previous figures.

FIG. 17 illustrates an example of releasable electric connectors which can be used in combination with the releasable connection means.

FIG. 18 is a block diagram of the software and hardware structure of the portable ultrasound system.

DETAILED DESCRIPTION OF EMBODIMENTS OF THE INVENTION

Figure 1:
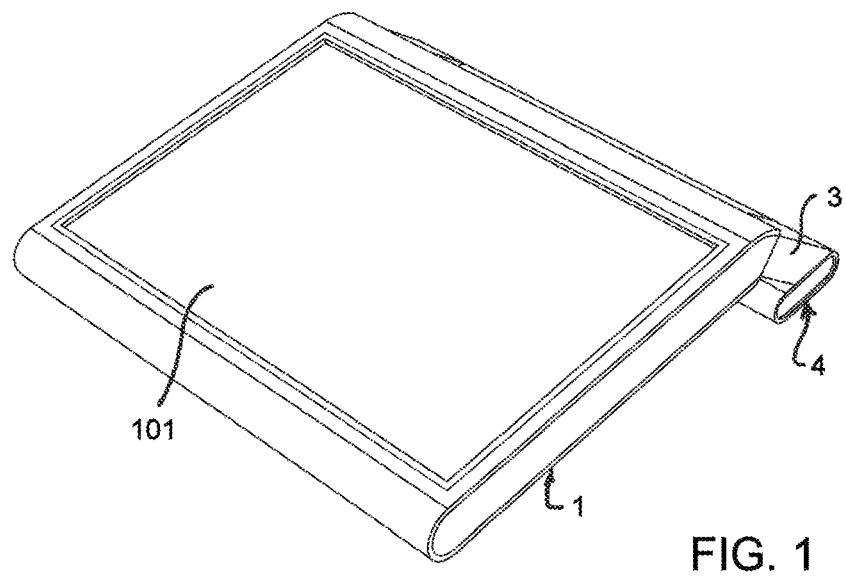
FIG. 1 is a perspective view of the main unit of an ultrasound system according to the present invention while lying on a table and in its simplest configuration as a tablet PC.

Referring to FIGS. 1 to 4, a portable ultrasound system comprises a main unit and a probe 2 which is connected to the main unit by means of a cable 5.

The probe 2 and the cable 5 can be connected to the main unit by means of usual connectors, which are not illustrated in detail since these connectors are known and widely used for connecting ultrasound probes.

The main unit comprises the hardware and software and the peripherals, which are necessary for driving the probe 2 to transmit ultrasound beams in a body under examination and to receive ultrasound beams from the body, and which are necessary for processing the received signals in order to generate diagnostic images of the inner parts of the body under examination.

The hardware of the main unit is housed in a case 1 which has the form of a so called portable tablet PC. In particular, the case is formed by a thin parallelepiped case having a front and a back side which are the largest sides. The front side is formed approximately entirely by a flat screen, particularly a LCD touch screen, 101.

In the illustrated example, the front and the back sides are rectangular. Although this is the preferred embodiment, the invention is not intended to be limited to the present rectangular form.

The lateral sides connecting the front and the back sides are the smaller sides of the case.

Two arms 3 protruding from two corners at the ends of one lateral side carry at their ends an elongated member 4. These two arms departs from the opposite ends of one lateral side or from an edge of the back side or from two opposite lateral sides and are oriented in the direction of the back-side of the case 1 and protrude backwards of the back side, terminating at a certain distance from the back side. Thus, the elongated member lies at a certain distance backwards relative to the back side of the case 1 of the main unit.

Preferably, the two arms 3 have identical lengths, so that the elongated member is positioned parallel to the back side of the case and also parallel to one edge of the back side.

In the present example, the elongated member is parallel to the longer side of the rectangular back side of the case.

Furthermore, the two arms are inclined in such a way that the elongated member is carried also in a position in which the elongated member is laterally spaced from the lateral edge of the back side of the cage, so that the elongated member does fall outside the boundaries of the back side.

Figure 3:
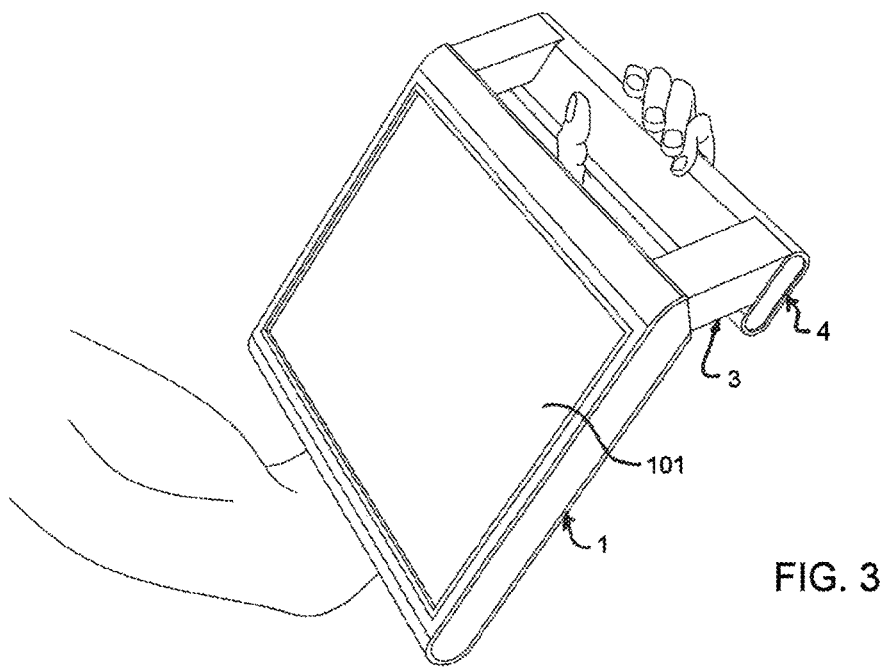
FIG. 3 illustrates a first condition of holding the main unit during use and with a panoramic orientation of the screen.
Figure 4:
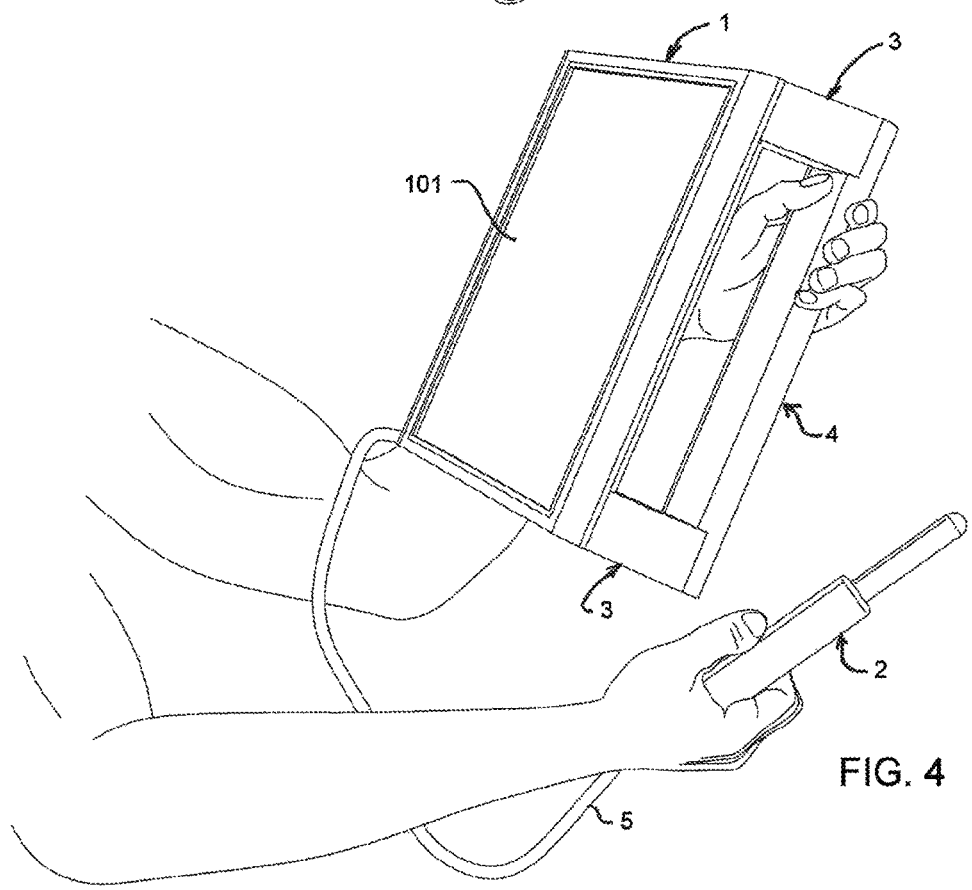
FIG. 4 illustrates a second condition of holding the main unit during use and with a portrait orientation of the screen.
Figure 5:
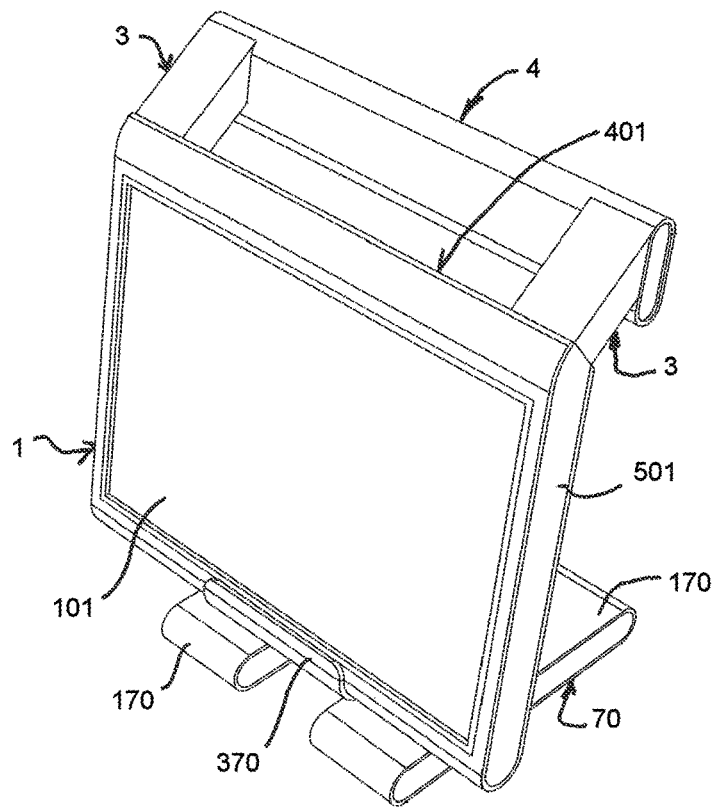
FIGS. 5 to 8 illustrate several views of the combination of the main unit and of a main unit table support, which allows positioning the main unit to have the screen approximately in a vertical position, while in FIG. 8 the main unit is separated from the support.
Figure 6:
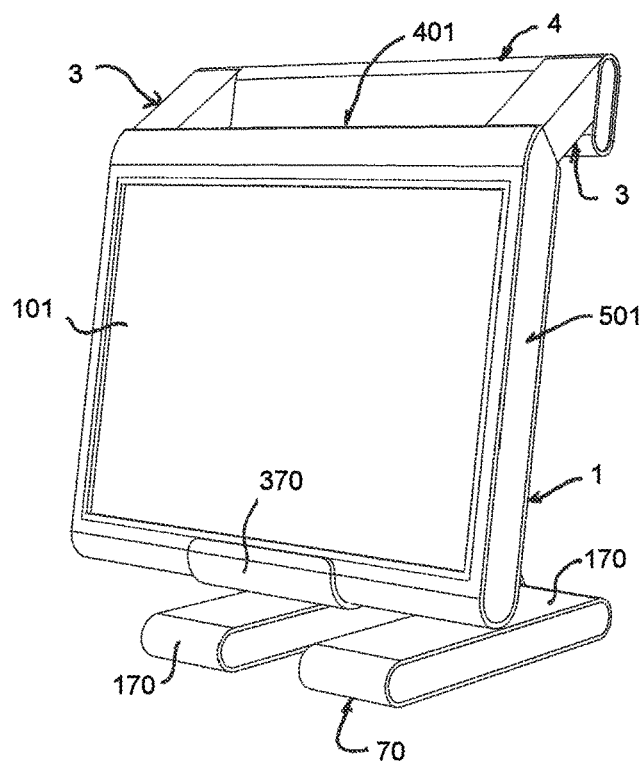
Figure 7:
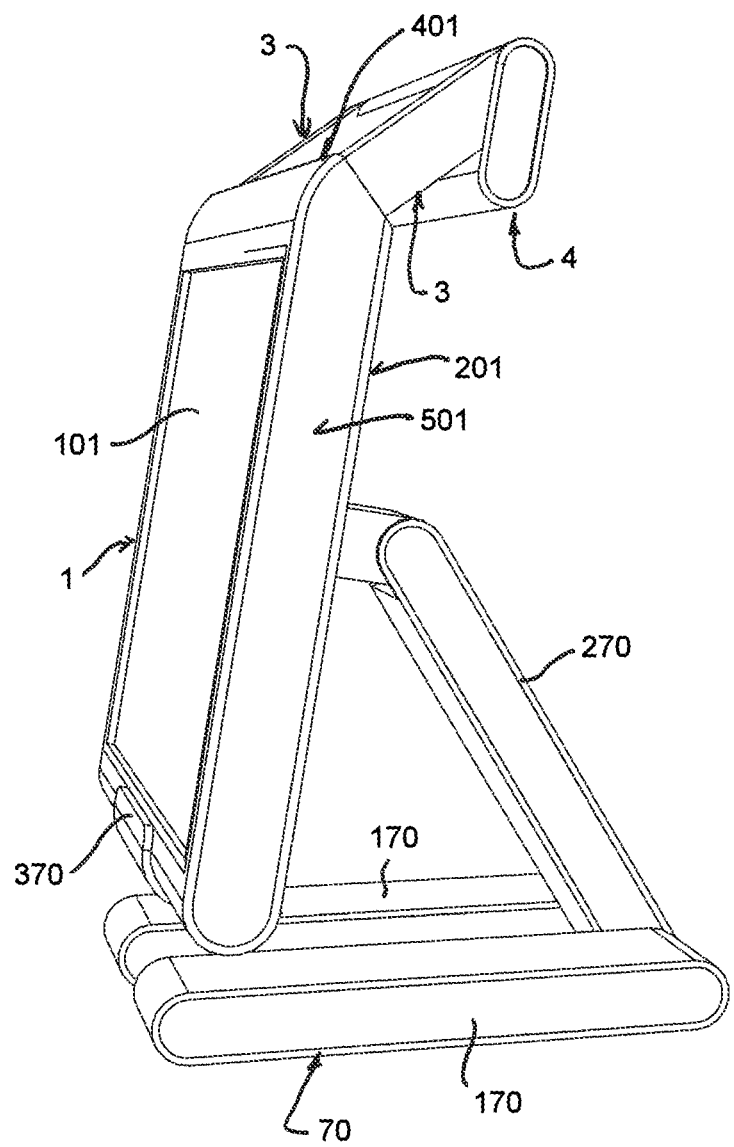
Figure 8:
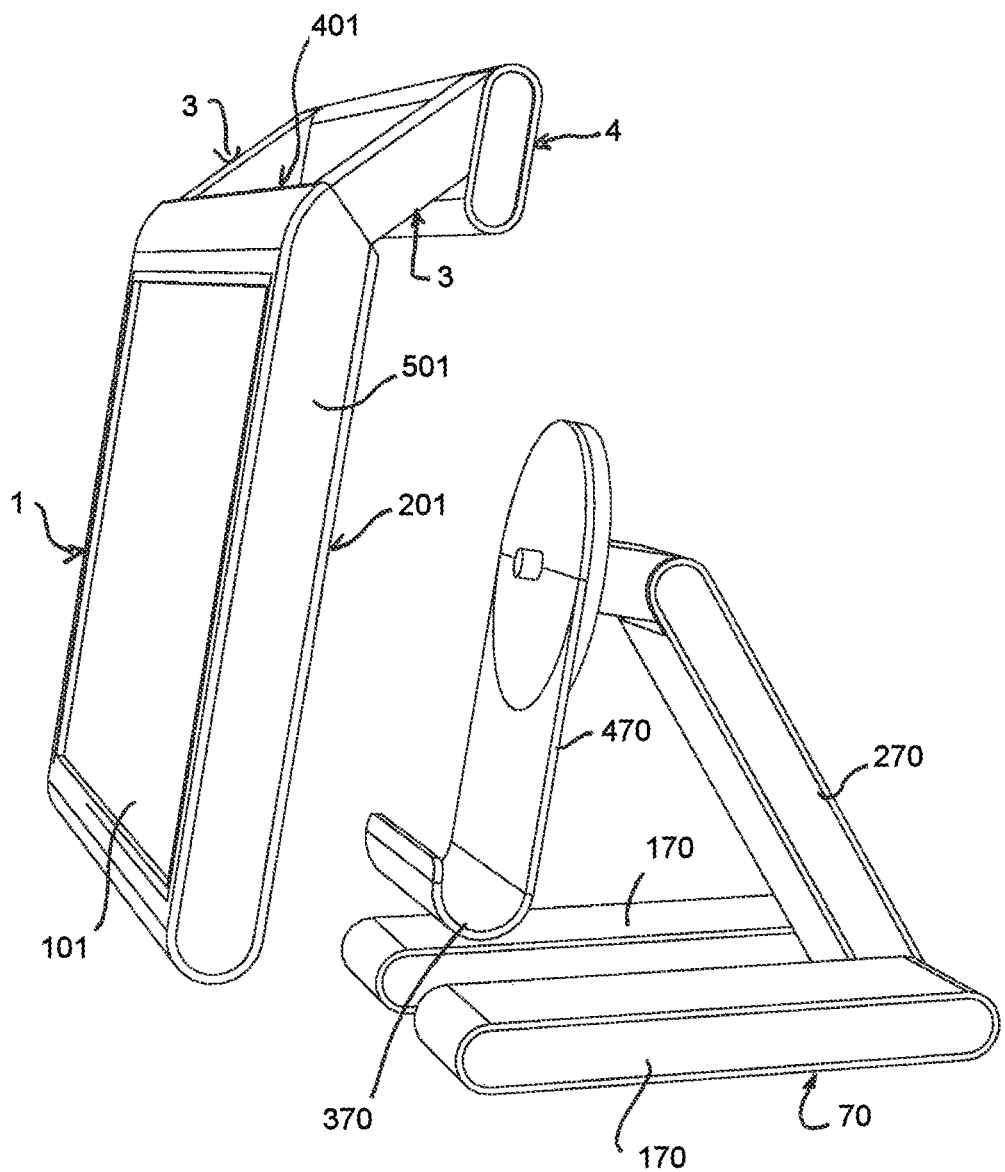

The elongated member has a cross section which can be grasped and held by one hand as illustrated in FIGS. 3 and 4.

Figure 2:
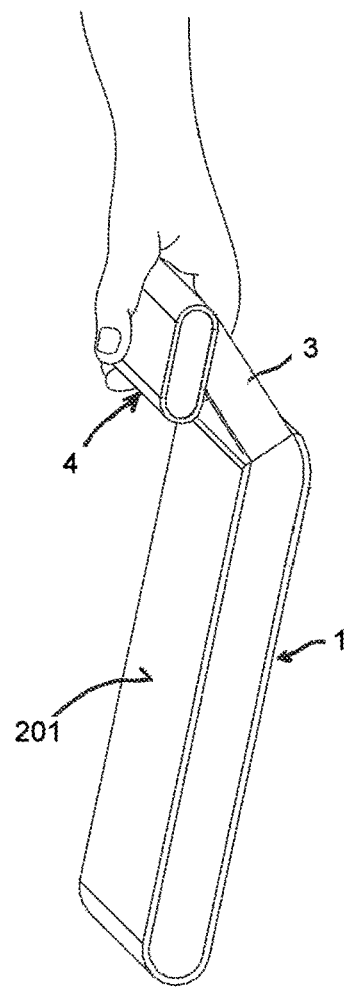
FIG. 2 illustrates the main unit of FIG. 1 while transported as a brief case.

As it appears from FIGS. 1 to 4, the particular configuration of the elongated member and its position relative to the case 1 of the main unit allow the handle to have several functions. As illustrated in FIG. 1, the elongated member 4 has the function of holding the case inclined when it is placed on a table, so that the screen at the front side 101 of the case is inclined in a way ameliorating the sight of the screen. As illustrated in FIG. 2, the elongated member serves as a handle for carrying the ultrasound system in a way similar to a briefcase.

As illustrated in FIGS. 3 and 4, the elongated member 4 serves as a handle for blocking the case of the main unit in place and supporting the weight of the case by means of the same arm, the hand of which is grasping the elongated member 4.

According to a preferred embodiment, the length and the width of the case 1, i.e. the lengths of the edges of the front and back side of the case 1, are such that they are not longer than the mean length of the forearm, approximately from the wrist to the hollow of the elbow.

This provides that, when the front and back sides are rectangular, the case 1 can be held either in the portrait or in the landscape orientation of the rectangular monitor. When the configuration of the main unit is such that the elongated member is positioned parallel to the longer side of the front and back side of the case, then when the hand holds the elongated member horizontally or approximately horizontally, the monitor has a landscape orientation and the longest side of the case opposite to the one at the elongated member rests on the forearm.

In FIG. 4, the hand holds the elongated member 4 in a vertical plane and the monitor has a portrait orientation, which means with the longest side in a vertical direction or in a vertical plane, while the lower shorter side of the case, which is parallel to the lower shorter edge of the monitor, rests on the forearm. In the configuration of FIG. 3, the arm is oriented along a direction which is approximately parallel to an axis which is perpendicular to the elongated member and parallel to the back side. Preferably, the forearm is approximately coincident with the central axis of the back side, which axis is perpendicular to the elongated member 4.

In FIG. 4, the arm is oriented approximately along a diagonal of the back side of the case 1.

Figure 9:
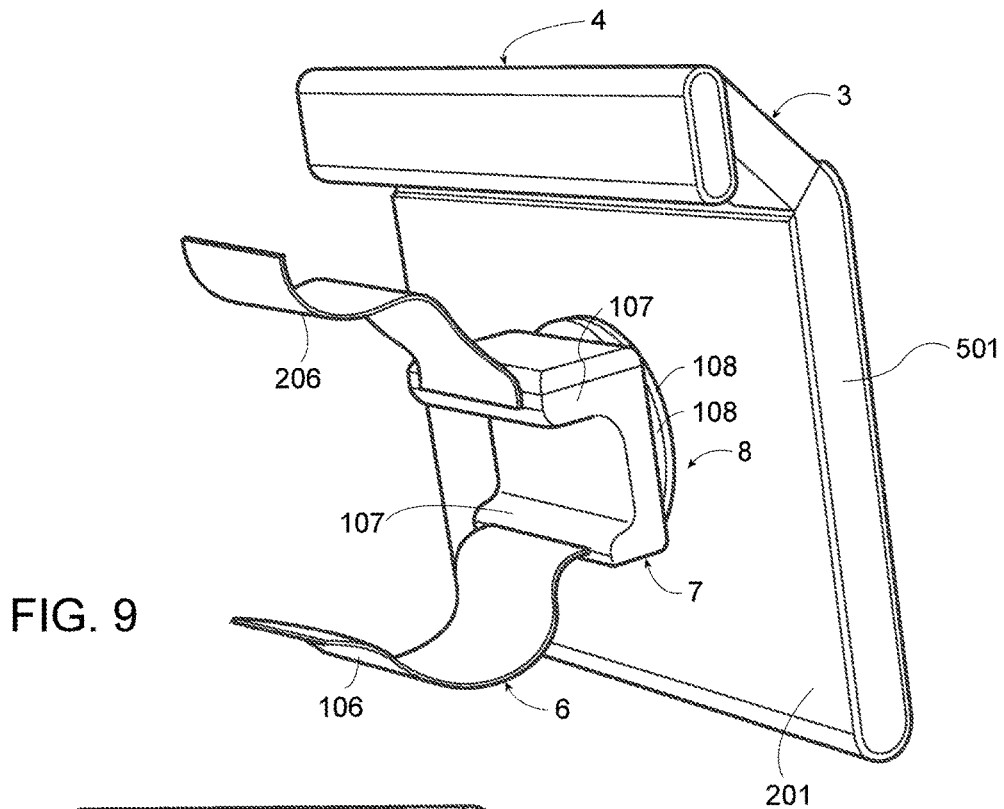
FIGS. 9 and 9A illustrate the backside of the main unit to which a saddle like contact part is attached for securing the main unit to the arm, leaving the hand free from grasping the handle.

As it appears from FIG. 9, according to a variant embodiment, the case 1 may be provided on its back side 201 with means for securing the case to the fore arm.

The simple means that can be provided are one or more parallel straps that can be tightened around the forearm. For example, a strap 6 having a certain width has two ends 106, 206 which carry means for connecting together the two ends and for tightening the strap. These means can be for example of the kind of the so called velcro tape, a hook and loop tape, one part of which is provided on one end 106 and the other part of the velcro strap is provided on the other end 206 of the strap 6.

Other kinds of connecting and tightening devices can be provided as for example the means used for the straps of the diving masks or for the belts of the backpacks.

Because the back side 201 of the case 1 is flat, according to another feature, the strap or the straps 6 are provided in combination with an anatomical contact part 7. This part is illustrated in FIG. 9 and is of the saddle like kind, having a U shaped cross section and a form and dimensions allowing the forearm to fit therein at least for a part of its cross section. The ends of the strap 6 departs each one from one of the arms 107 of the U cross section of the saddle like contact part.

Figure 9A:
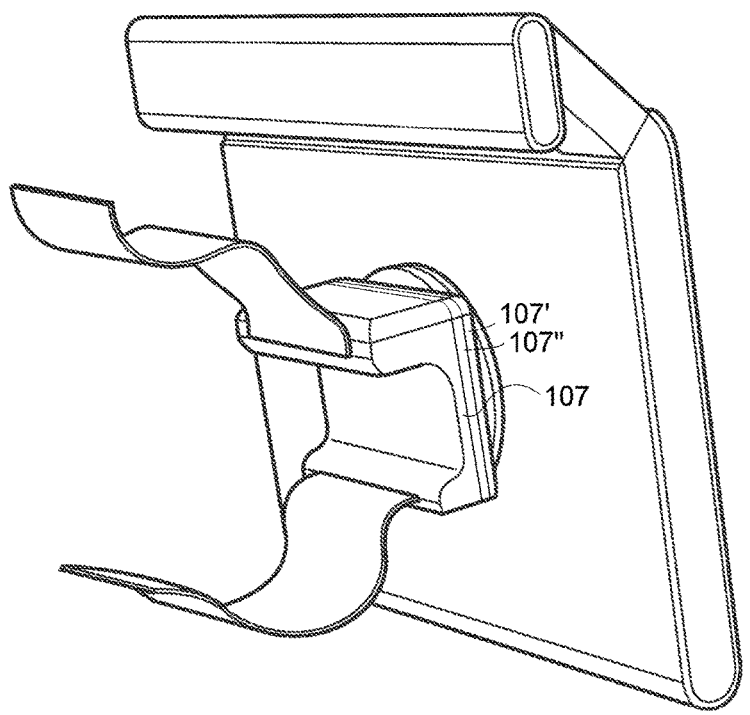

According to an additional feature, the saddle like contact part 7 is secured to the back side 201 of the case 1 by means of a device allowing its rotation along an axis perpendicular to the back side 201. In particular the rotation axis of the saddle like contact part coincides with the central axis perpendicular to the back side 201 of the case 1. Many ways can be provided for allowing a rotation of the saddle like contact part 7. One example of device 8 for allowing the rotation of the saddle like contact part 7 is illustrated in FIG. 9 and has two circular plates 108 secured together at their center in such a way that the two plates can rotate one relative to the other. One plate is secured to the back side 201 of the case while the other plate is secured to the saddle like contact part 7. Furthermore, between the two plated there can be provided means for provisionally stopping the two plates in certain angular positions one relative to the other. These means are not illustrated since many solutions are possible, which lie within the choice of the skilled person. As an example, one plate could be provided on a circular path coaxial with the axis of rotation with one or more notches or cuts which are distributed along the circular paths, while the other plate is provided on the same circular path with one or more balls, which are housed in a hole and which are pushed permanently with a certain force against the other plate by mean of an elastic element such as a helical spring. When during relative rotation, one with respect to the other, one of the balls is coincident with one of the notches, the rotation is stopped and can be continued only by applying a certain release force, which is needed in order to push back the ball in the hole and free again the movement of the plates. In addition, one or more additional cases (in the embodiment illustrated in FIG. 9A, two additional cases 107' and 107") may be interposed and connected between the saddle-like contact part 7 and the rear side of the case of the main unit.

Because the case can be secured tightly to the forearm, the hand must no more grasp tightly the elongated member and can merely ensure that the device will not slip away and fall down, or balance the device on the forearm. Thus the hand can be used to activate one or more keys or buttons or the like which may be present on the elongated member and which can be used for general purposes or for activating special functions during the execution of a scanning, so that the hand holding the probe 2 is not necessary and the examination must not be stopped for entering the command or control needed.

The elongated member is advantageously empty inside at least partially and is made in such a way that it provides the housing of one or more battery packs or other hardware.

Figure 21:
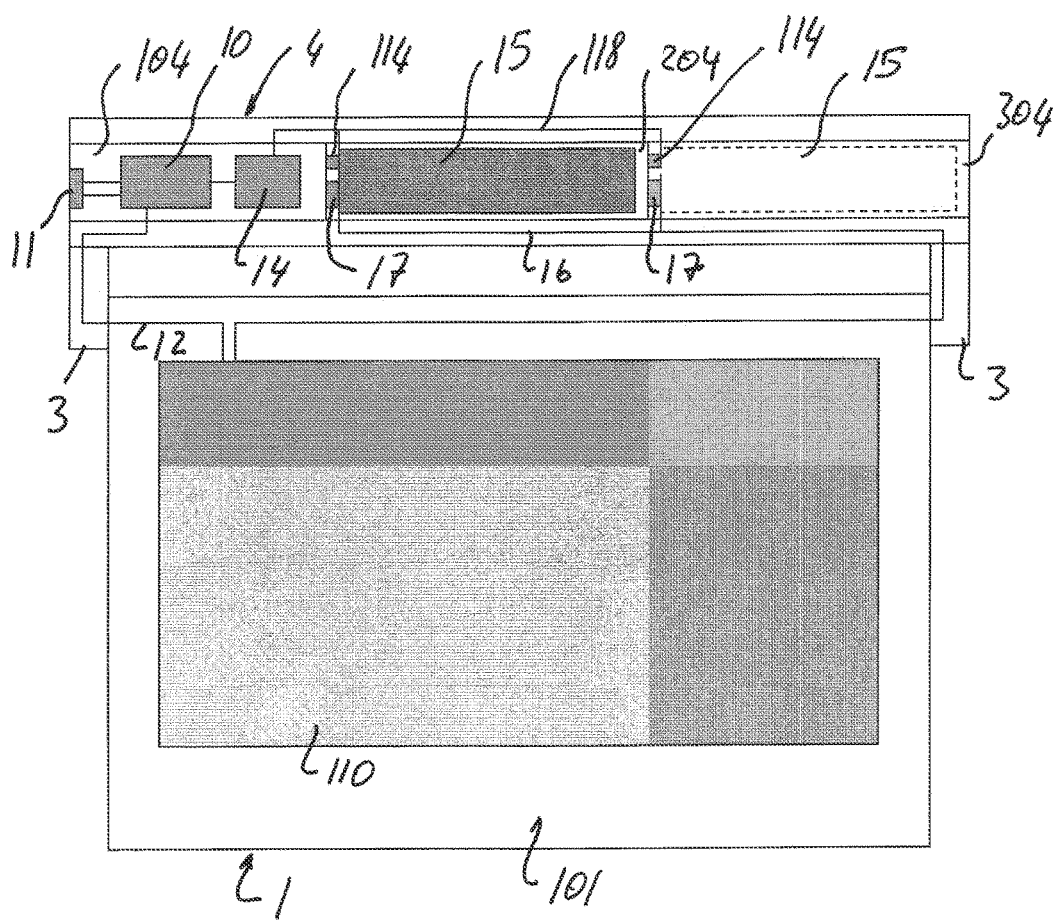
FIG. 21 is a schematic example of the lay-out of the elongated member which is void inside and has three chambers, one of which is for the power feeding circuit connecting the system to an external power source such as an electric network, and also for a recharging unit for the battery packs, while the other two chambers are each for housing each a battery pack.

An example of this construction is illustrated in FIG. 21. This figure is very schematic since the constructive arrangements are a matter falling within the technical general knowledge of the skilled person.

FIG. 21 represents only one example of several different configurations which are obvious once one configuration is disclosed.

The illustrated elongated member has three separate chambers. Chamber 104 is configured to house a power feeding circuit indicated with 10, which connects with its input to a connector 11 at one external side, particularly one head side of the elongated member 4. The output of the power feeding unit 10 is connected to the hardware indicated by 110 in the case 1 by means of a power feeding line 12, which passes from the elongated member 4 inside the case 1, by passing through one arm 3 connecting the elongated member 4 to the case 1. In the same chamber 104 or in another separated chamber (not illustrated) one more circuit can be provided, which can be for example a battery charger 14. The battery charger 14 can be fed with power by the power feeding unit 10, while its output is connected to a charging connector 114 provided in each of two battery packs housing chambers 204, 304. In this case, it is assumed that the battery packs 15 have charging inputs and power outputs which are separated and for which in the corresponding housing 204, 304, there are provided connectors 114 and 17 for automatically connecting a charging line 118 and a power feeding line 16 to the charging input and to the power feeding output of the battery pack 15 when it is inserted in the corresponding chamber 204, 304.

In the present example the two chambers 204, 304 can each house a battery pack independently one from the other. So the ultrasound system has two so called battery bays in which a battery pack can be inserted independently regardless of whether a battery pack is present or not in the other bay.

An alternative configuration may consist in that the power feeding unit and the charger are external devices as in the presently known notebook computers, while the chamber 104 is an additional battery housing.

The chamber 204, 304 are constructed to house more than one battery pack 15.

The chambers 104, 204, 304 have an open side through which they can be accessed. A cover can be provided for each of the chambers. There might be provided that the cover is for closing the open side of all or of part of the chambers.

A further alternative which can be provided consist in that the battery packs 15 are stably housed inside the elongated member 4 and cannot be separated therefrom. When the battery packs have to be substituted, the entire elongated member has to be substituted. In this case, the elongated member can be secured to the case 1 or to the two arms 3 in a releasable manner.

In another variant embodiment, the elongated member 4 forms chambers for housing battery packs or hardware. These housings can be accessed for substituting the battery packs or the hardware and may be provided with an elongated member which is releasable from the case or from the two arms 3. This may be important for changing the elongated member in order to mount one elongated member which can house more battery packs or which has different configuration of keys on it or which has different hardware housed in it.

Several different examples are illustrated in FIGS. 12 to 15 and 19 and 10.

In FIGS. 12 to 15, the two arms 3 which support the elongated member 4 in a cantilevered way from the case 1 of the main unit have two terminal protrusions 103 at the end opposite to the one connected to the elongated member. Each protrusion is provided with a passing hole 203. The case 1 of the main unit has at each end of its upper lateral side 401, parallel to which the elongated member 4 has to be held, an opening for accessing a pocket which extends parallel to the lateral side 501 perpendicular to the one 401 parallel to which the elongated member 4 has to be held. That pocket is dimensioned such that the corresponding protrusion 103 can be inserted therein. The walls forming the lateral sides 501 have a passing hole coinciding with the hole 203 of the protrusion 103. That hole can pass the pocket from side to side to be provided into both walls delimiting the pocket, one of which walls is formed by the wall of the lateral side 501 of the case 1. The hole can be threaded along its entire length or only for the part provided in the lateral wall of the pocket which is internal to the case 1. Alternatively the hole 203 in the protrusion 103 is threaded. A screw 20 is provided for being screwed into the hole in the lateral walls of the pocket or in the hole 203 of the protrusion 103 of the arm carrying the elongated member 4.

The electric lines for feeding the power signal from the power feeding unit, and/or from the battery packs in the elongated member, and/or for feeding other signals from other hardware provided in or on the elongated member 4 to the hardware in the case of the main unit, as illustrated diagrammatically in FIG. 21, may pass from the elongated member 4 into the case 1 through the arms 3. In the examples depicted in FIGS. 12 to 15, the arm has a bigger cross section than the one of the protrusions 103 and is made tubular. The ends 303 may carry or be conformed as an electric multipolar connector part cooperating with a complementary electric, multipolar connector part, which is carried at the lateral side 401 parallel to the elongated member beside the corresponding pocket for the protrusion 103 of each of the arm 3.

The connector parts engage each other automatically when the protrusions 103 are inserted in the pockets and are disconnected automatically when the elongated member 4 with the arms 3 is separated from the case 1 of the main unit.

The particular construction of the connector is not illustrated since there are currently available a very large number of electric connectors which can achieve the above function and the skilled person only has to make a choice between the available connectors.

Figure 19:
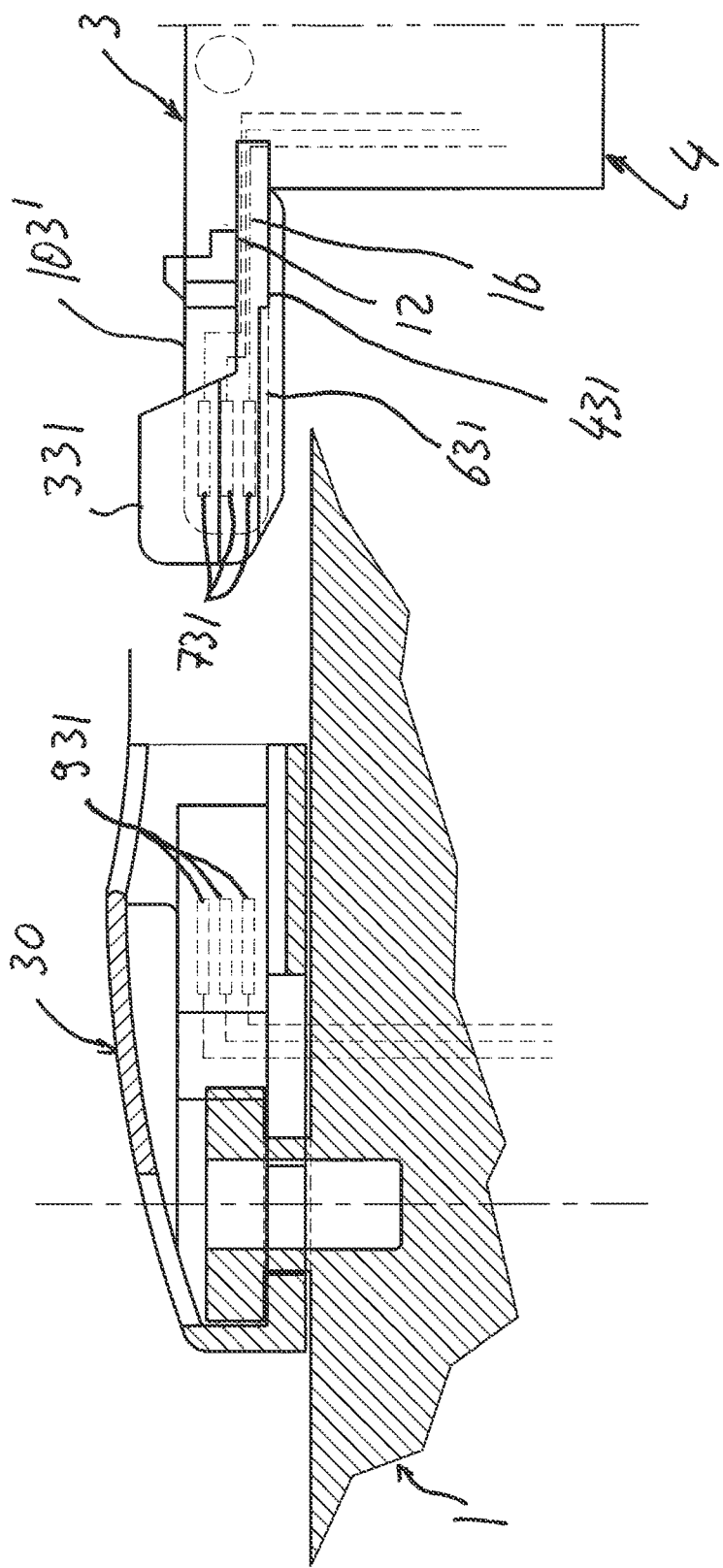
FIG. 19 and FIG. 20 illustrate an example of a particular embodiment of the connector which secures the elongated member to the case of the main unit, and also an example of the therein integrated conductors for feeding the power signal to the main unit and or for feeding other electric signals generated for example by keys or buttons or similar devices provided on the elongated member.
Figure 20:
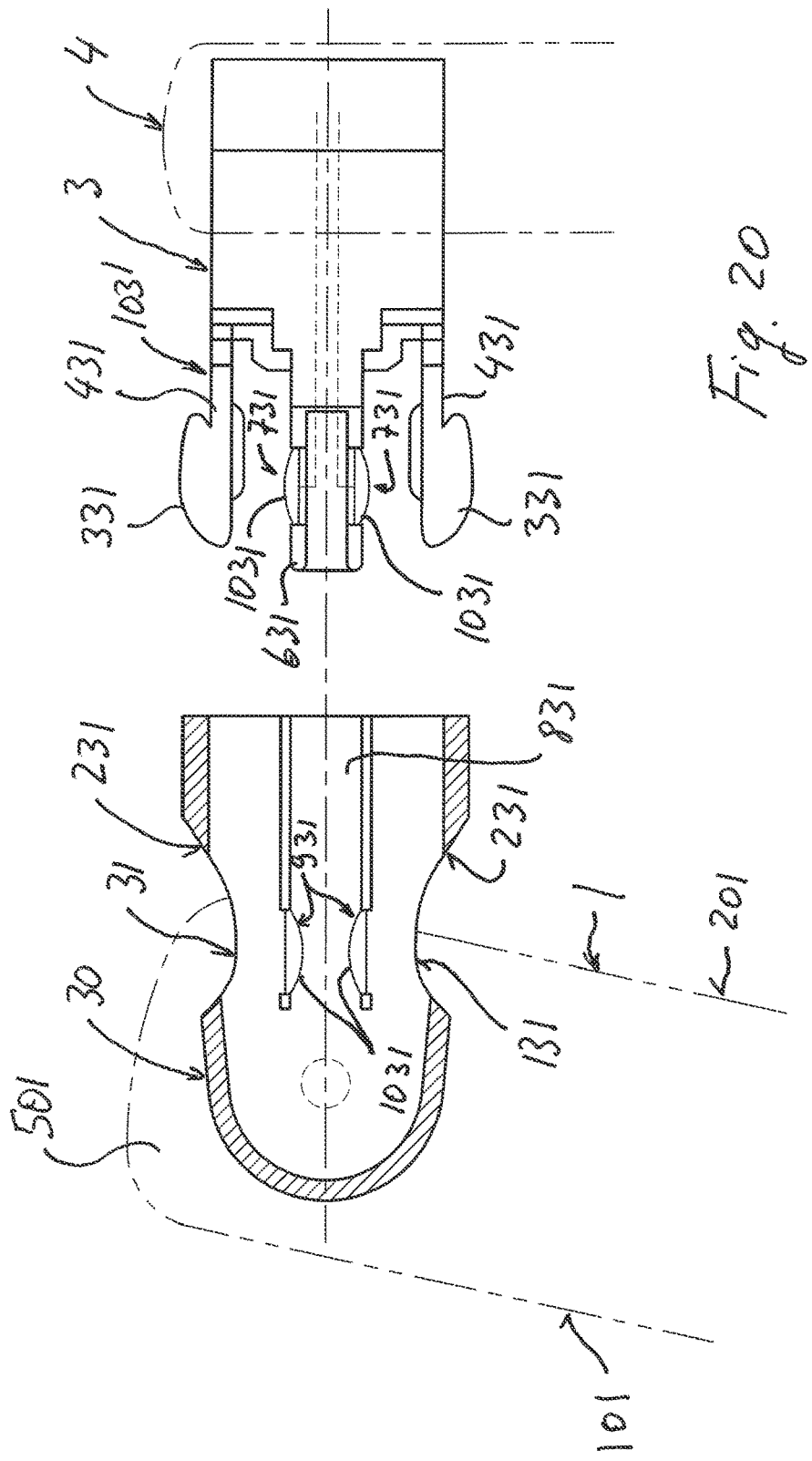

FIGS. 19 and 20 show a detail which is an alternative to the above embodiment. Here the connection between the arms 3 carrying the elongated member 4 and the case 1 are of the snap-in type.

Also in this case there could be plenty of constructions and the one of FIGS. 19 and 20 represents only one example. In this example the connection is of the kind known for example for belts or for shoulder straps of a back packs or for the securing straps of professional fins having an open shoe part.

A pocket like part 30 is secured to each wall of the opposed lateral sides 501 oriented perpendicular to the elongated member 4 and parallel to the arms 3. The pocket has an opening which is oriented towards the arms 3. Each arm 3 has a protrusion 103' which is configured to be inserted in the pocket-like part 30.

The pocket like part 30 has two openings 131 in each of its lateral sides which are perpendicular to the side 501 to which they are secured. The openings form an engaging edge 231 for a corresponding engaging tooth 331 which is carried at the end of an elastic tongue 431 of the protrusion 103'. The protrusion has two elastic tongues 431, which are oriented parallel to the direction of insertion in the pocket 30 and which are eccentric and symmetrically positioned relatively to a central longitudinal axis of the protrusion, which is a central axis parallel to the direction of insertion in the protrusion 103' in the pocket part 30. Each elastic tongue 431 is flexible in a direction perpendicular to the longitudinal central axis and against the longitudinal central axis, and carries the tooth 331 on its lateral side facing the lateral side of the pocket part 31. In their normal rest position, the tongues are oriented in such a way that the rear fronts of the teeth are aligned with the engaging edge 231 of the openings 131 in the lateral sides of the pocket part 30. The end of each tooth is beveled in such a way as to form a sliding surface of the lateral side of the opening of the pocket part 30 along the tooth, so that automatically the tongues 431 are bent one against the other allowing the protrusion 103' to enter the pocket like part 30 and slide therein till each one of the two teeth 331 are coincident with the corresponding opening 131 in the lateral wall of the pocket like part and the tongues are free to spring up laterally outwards. Thereby, each tooth is automatically engaged in the opening 131 and its rear side is aligned with the retaining edge 231 of the corresponding opening 131.

For freeing the protrusion 103' it is sufficient to press, with the hands, the teeth one against the other and displace them below the retaining edge so that the protrusion 103' can slip out from the pocket.

A particular multipolar electric connector can be provided in combination with this kind of mechanical connector. The protrusion 103' has a central longitudinal element 631, and one of the lateral outer walls or both the lateral outer walls of the longitudinal element 631 carry several longitudinal electric contacts 731, each connected to a conductor which passes inside the central longitudinal element 631 and through the corresponding arm 3 inside the elongated member 4. The pocket like part 30 is provided with a central guide 831 for the central longitudinal element 631, which central guide is channel like and has lateral walls, each carrying a corresponding number of electric contacts 931 in such a position that each contact will be coincident and will be in contact with a corresponding electric contact 731 on the central longitudinal element 631 of the protrusion 103' when the protrusion 103' is inserted in the pocket like part 30 with its end position. Each contact 931 is connected to the hardware in the case 1 by means of a conductor passing inside the case 1 through passages in the pocket like part 31 and in the lateral wall 501 to which this part is secured.

Advantageously, as shown in the drawings, the electric contacts 731 and 931 are of the kind having an elastic contact terminal 1031, which is urged elastically in a position protruding outwards from the surface of the central longitudinal element 631 and from the lateral walls of the central guiding channel 831 in which the central longitudinal element 631 of the protrusion 103' of the arm 3 slides when the protrusion is inserted in the pocket like part 30. These protruding elastic contact terminals 1031 can have an arched form, so that they are invited to slide one over the other when the electric contacts 731 and 931 come to slide one over the other.

As it appears from FIGS. 12 to 15, the present releasable elongated member 4 allows providing different kinds of elongated elements having the same arms 3 and the same kind of protrusions 103, 103' so that different kinds of elongated elements 4 can be mounted on the case 1.

Figure 13:
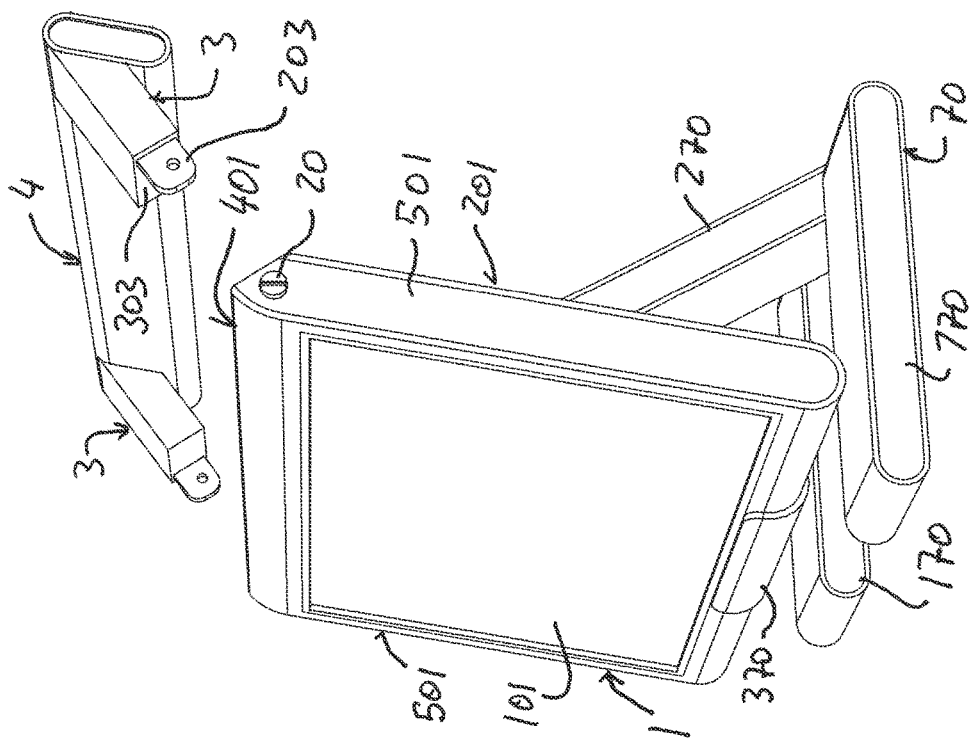
FIGS. 12 and 13 illustrate a variant embodiment in which the elongated member together with the two supporting arms are releasably secured to the case of the main unit.
Figure 12:
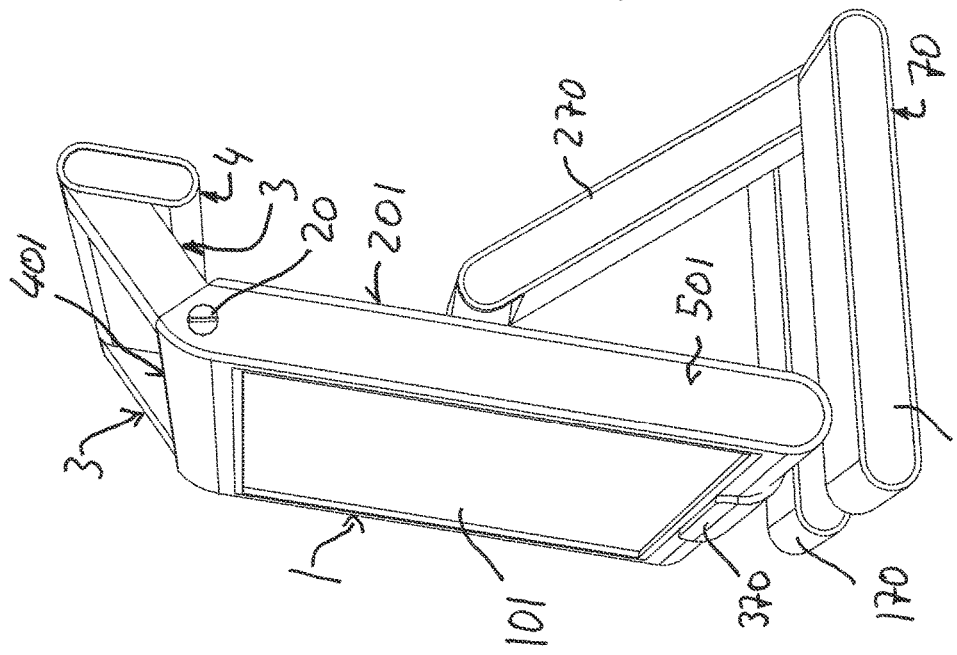

Here, for example, the two elongated elements 4 of FIGS. 12 and 13 and of FIGS. 14 and 15 differ one from the other in that they have different cross sections. The elongated element of FIGS. 14 and 15 has a cross section which is approximately double in size of the area than the cross section of the elongated member of FIGS. 12 and 13. This allows having a bigger number of chambers or a bigger chamber for housing more battery packs and/or more hardware in the elongated member 4, and/or also more keys or buttons or commands. When a long endurance of the battery packs is not needed, the thinner elongated element 4 can be mounted on the case. When more endurance or more power is needed, the thicker elongated member can be mounted on the case. Also, if different additional functions such as for example communication hardware and/or additional driver units for writing and reading memory supports or additional hard disks units or other devices are needed, a particularly configured elongated member carrying the additional devices can be mounted on the case 1.

Figure 10:
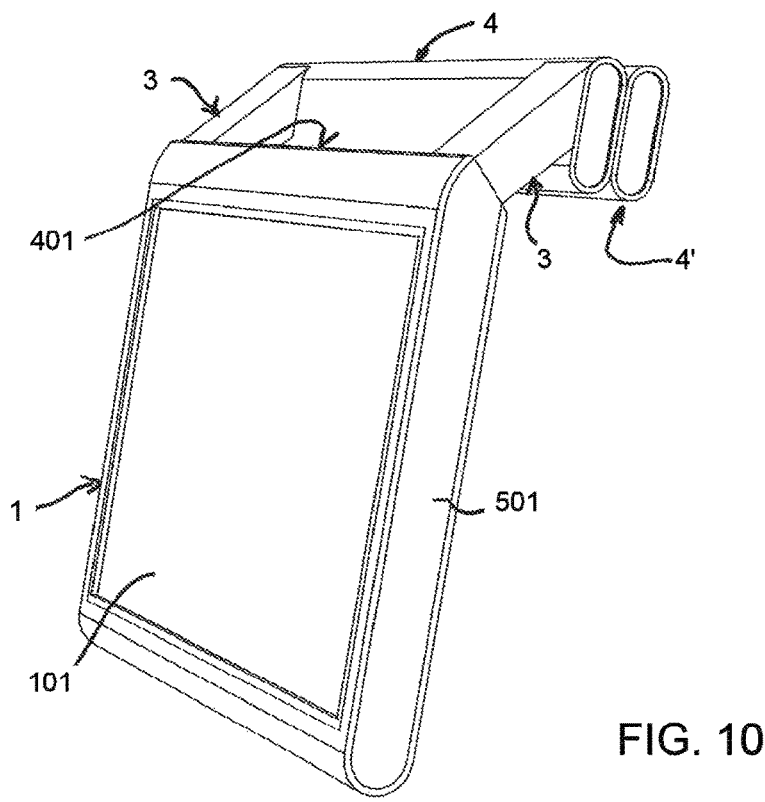
FIG. 10 illustrates a variant embodiment in which the elongated member forming the handle is doubled by attaching a second elongated member to the first one.
Figure 11:
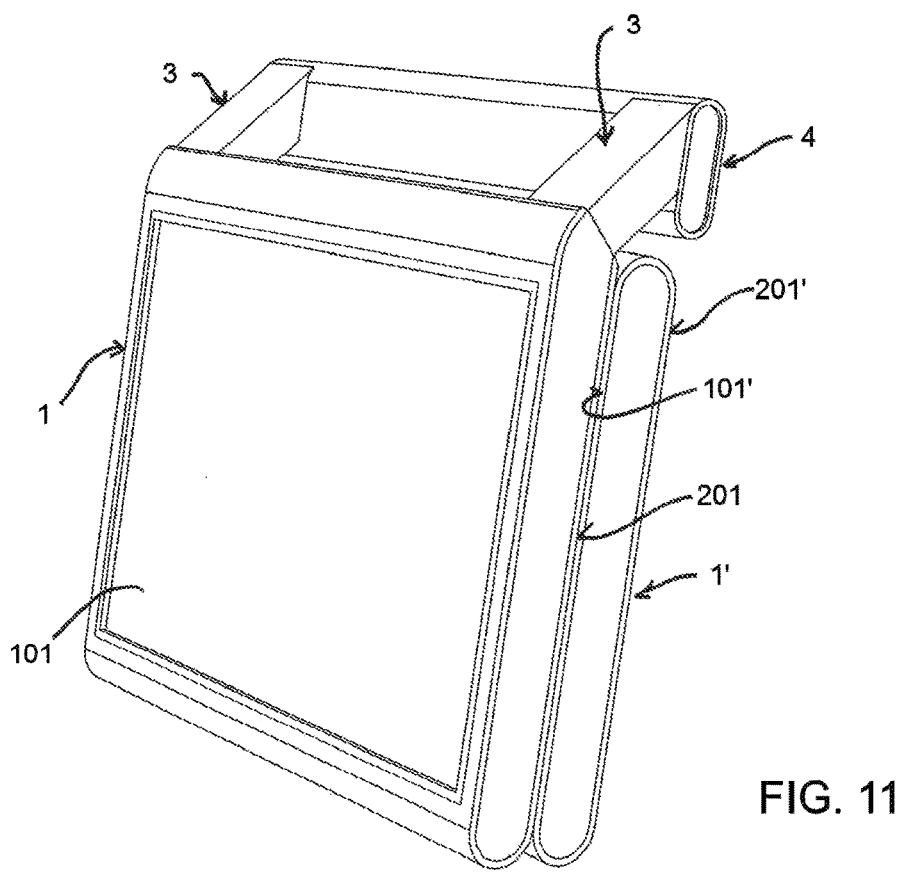
FIG. 11 illustrates a variant embodiment in which the main unit is attached with its back side to a docking unit.

According to a further embodiment of an ultrasound system according to the invention, which is illustrated in FIG. 10, a second elongated member 4' can be attached to a first elongated member 4, which is attached to the case 1 by means of the arms 3 either in a stable or in a detachable or releasable manner as described above. The second elongated member 4' serves as a case for further battery packs or further hardware according to the different constructions disclosed above for the first elongated member 4. In this case, the power feeding lines, and/or other communication lines of the hardware housed in the second elongated member 4' for connecting the battery packs, and/or the hardware housed in the second elongated member in the case of the main unit, passes through the first elongated member 4. This is done by means of an electric connector of the kind used for connecting a docking station with its notebook computer. In particular a two part connector is provided, a first of the connector parts being provided on the side of the first elongated member 4 against which a facing side of the second elongate member 4' comes into contact when the second elongated member is attached to the first one. A second connector part is provided on the side of the second elongated member facing the side of the first elongated member 4, against which the second elongated member 4' comes into contact with the first elongated member 4.

Particularly advantageous is a connector as the one illustrated in FIG. 17. Here the side 604 of the first elongated member 4 has a slot 704, in which a plurality of contact terminals 804 are aligned forming a row of contacts which are oriented with their surfaces of contact to the contact terminals 804' of the second elongated member in a plane perpendicular to the side 604 of the first elongated member 4, i.e. perpendicular to the side of the first elongated member against which a facing side 604' of the second elongated member 4' is brought in contact when the two elongated members are attached one to the other.

The second elongated member 4' is provided, in a position coincident with the slot, with a connector plate 704' carrying a row of contact terminals 804'. The contact terminals 804' are oriented parallel with the contact terminals 804 of the connector part provided on the first elongated member 4 and laterally shifted in such a way that each of the contact terminals in the slot 704 of the first elongated member 4 will slide against a corresponding contact terminal 804' on the connector plate protruding out of the side 604' of the second elongated member 4'. The contact plate 704' is parallel to the slot and to the surface in the slot 704 carrying the row of contact terminals 804. Each contact terminal 804, 804' can be further formed by a flexible tongue which is arched along an axis perpendicular to the direction of engagement of the contact plate 704' in the slot 704. The arched tongues of the contact terminals 804 in the slot protrude in the direction of the arched contact terminals 804' on the connector plate 704' of the second elongated member 4' such that the arched tongues of the contact terminals 804 and the one of the contact terminals 804' interfere one against the other, so that each contact terminal 804 and the corresponding contact terminal 804' are pressed elastically one against the other in the engaged condition of the two parts of connector.

When the second elongated member is brought against the first elongated member 4 by aligning the two connector parts, they will be automatically engaged one in the other.

The first elongated member 4 can be provided with an additional power line for the additional battery packs of the second elongated member 4', or the output of the power lines in the second elongated member can be connected to the power lines of the first elongated member 4 so that an extension of the already present power line network is generated.

Similarly the communication lines of the additional hardware housed in the second elongated member can be connected to separate communication lines already provided in the first elongated member 4, which are dedicated to the additional hardware, or the communication lines provided in the second elongated member 4' can be connected with the communication lines of the first elongated member 4 forming an extension of a communication network which is common to every additional hardware in both of the two elongated members 4, 4'.

It is to be noted that not only two elongated members 4, 4' can be attached one to the other mechanically and electrically, but also three or more additional elongated members can be attached in a cascade one to the other and to the first elongated member.

The mechanical attachment can be made by means of releasable means such as the ones illustrated as an example in FIG. 16. One of the two elongated members, and in particular the second or a further one 4', carries on the side to be brought into contact with a side of the first elongated member 4 a hook 40, which is provided on a pin 41 protruding perpendicularly out of a housing 42 through an opening of the housing, on the side of the second elongated member 4' designed to come into contact with a side of the first elongated member 4. The pin 41 is carried by a cursor 43, which is mounted slidably in a guide 44. The guide 44 is oriented with its longitudinal axis perpendicular to one of the head sides of the elongated member, where it is open, allowing the end of the cursor 43 to protrude out of the opening and to operable by mean of the fingers. An elastic element maintains the cursor 43 in a position in which it protrudes out of the opening of the guide 44, and the hook 40 at the end of the pin 41 is in a position of engagement of a retaining edge 45, which is formed by an undercut in a lateral wall of a notch 46. The notch 46 is provided in the side wall of the first elongated member 4 designed to be brought into contact with a wall of the second elongated member 4' when the two elongated members are attached one to the other. The notch 46 and the hook 40 are provided in coincident positions when the two elongated members are attached one to the other. The hook preferably has a rounded head, which helps in being automatically driven to engage the retaining edge 45 when the two elongated members 4, 4' are brought with their facing sides into contact one with respect to the other.

In order to release the two elongated members one from the other, the hook 40 can be disengaged from the retaining edge 45 of the slot 46 by pushing on the head of the cursor 43 protruding out of the opening of the sliding guide 44.

The above description is merely an example for demonstrating that mechanical releasable attachment means can be provided for connecting mechanically the two elongated members one to the other.

The second elongated member 4' can have the same form as the first elongated member 4.

A further variant embodiment, which can be provided separately or in combination with any of the previously disclosed combinations of features, consist in the provision of a second case 1' which has the form and the dimensions of the case 1 of the main unit and which further has the function of providing additional housings for more battery packs and/or additional housing for more hardware.

Despite the shape and the dimensions, which are such that the second case 1' can be releasable attached with its front side 101' to backside 201 of the case 1 of the main unit, similar features can be provided for this second case 1' as those disclosed for the second elongated member 4'. Indeed, the way and the construction, which apply for connecting mechanically one case to the other and for generating electric connections of the battery packs of the additional case 1' and/or of the additional hardware to the hardware of the main unit housed in the case 1, can be the same as those disclosed by means of FIGS. 16 and 17 for the second elongated member. Relative to the construction of the additional case 1', with reference to the housings for the battery packs and for additional hardware, similar features can be provided as those illustrated and described for the elongated members in FIG. 21.

The present embodiment further enhances the possibilities and flexibility of the configuration of the device relative to the endurance of the power supply and to its weight.

Similarly to the construction of the elongated member 4, more than only one additional case 1 can be provided. Each of the additional cases carry the hook means on one side and the notches on the other side, so that a second additional case can be attached to the back side 201' of a first additional case, which in turn is attached to the case 1 of the main unit.

In still another embodiment, the saddle like contact part 7 can be secured to the back side of the case in a releasable way thanks to releasable attachment means which can be of any kind, being many different attachment means known to the skilled person.

This allows connecting the case 1 to several other supporting devices, which enables a correct or optimized positioning of the device.

With reference to FIGS. 5 to 8 and 12 to 15, a table base 70 is provided in combination with the case 1 of the main unit, which allows positioning the case 1 with the front side formed by the monitor screen substantially in a vertical position. "Substantially" may mean, in this situation, a deviation between 0° to 30° from a vertical line. The table base has two horizontal feet 170, which are linked with one of their ends to the end of an intermediate supporting lever 270. At its end the supporting lever 270 carries a back plate 470, to which a lower supporting saddle 370 is secured in a rotatable manner around an axis which is perpendicular to the back plate 470. The lower supporting saddle 370 is provided at such radial distance from the axis of rotation that when the case 1 of the main unit is positioned with its lower horizontal side in the saddle 370, the axis of rotation is approximately coincident with the central axis perpendicular to the back side of the case 1. The saddle 370 extends till to the central area of the back side of the case 1, at which it is linked in the rotatable way to the back plate 470 and at which it has releasable connecting means to the back side of the case 1.

Thanks to this construction while lying on the table base, the case 1 can be freely rotated and the user is able to orient the monitor screen to a landscape or to a portrait position.

The hardware driving the monitor of the main unit can advantageously have automatic means for detecting the orientation of the screen of the monitor relative to the landscape or portrait orientation, which automatically adapts the image visualized on the screen to the orientation of the screen. These means are known and are for example gravity sensors.

Both in the case of the table base 70 and of the saddle like contact part 7, additional box like cases may be provided, which can be mounted releasably in an intermediate position between the back side of the case 1 and the side of the table base or of the saddle like connection part 7 facing the back side 201 of the case 1. Each box like case can carry different hardware or more battery packs. One or more of the box like cases can be provided such that a row of the one or more boxlike cases, secure one to the back of the other, is mounted to the back side of the case 1 and the row of box like cases and the table base or the saddle like connection part are attached.

Here the releasable way of fixing the intermediate boxlike cases can be the same as the one described above for the two or more elongated members 4, 4' or the two or more cases 1, 1' according to the configuration of FIGS. 10 and 11 and 16 and 17.

In another embodiment of the present invention, the portable ultrasound system has a completely graphical user interface. In this case the screen is of the touch screen kind and is able to receive commands by touching the screen with different control keys, buttons, switches and cursors in the form of graphic symbols representing the keys, buttons, switches and cursors. Selecting means are provided for selecting at least one specific application within a list of applications which are available on the portable echographic system, means being provided for loading and executing a specific graphic user interface program which generates on the screen the images of only the keys, buttons, switches and cursors that are needed for carrying out the tasks related to the selected specific application.

In a portable echographic system according to the invention, different electronic units for carrying out specific tasks are substituted by a central processing unit capable of executing different programs and of carrying out different tasks, at least a memory being provided in which there are saved different programs for controlling the central processing unit in order to carry out different specific tasks related to the functions of an echographic system. One or more of the different programs for carrying out specific tasks are loaded by the central processing unit and executed by it when a certain specific application has been selected by the user.

FIG. 18 is a simplified block diagram illustrating this structure. The structure is a typical hardware/software architecture. The hardware 80 comprises generic hardware 180 in the form of a processing section capable of memorizing and executing control programs. The control programs 281, 381, 481, 581 and 681 are of two kinds. Control programs 281 and 381 are general setup programs such as management programs or hardware configuration or setup programs. Control programs 481 to 681 are virtual ultrasound machines, in the sense that routines are provided which, when executed by the generic hardware and if necessary by a specific hardware drive, the generic hardware carries out specific imaging application oriented functions and activates the specific hardware if it is necessary for some very particular application specific functions. Furthermore each control program drives the touch screen to generate on it a graphic user interface, which comprises icons representing specific keys, buttons, cursors and other controls that are needed for the specific imaging application to which the virtual machine represented by the control program is directed. The keys, buttons, cursor icons and the eventually additional icons of other kind of manual controls can be activated manually by means of the touch screen in such a way to operate like the corresponding physical hardware devices.

So, for example, if only bi-dimensional B-mode imaging is needed, the main control program will be provided with a selection/activation function of a corresponding control program, which is loaded and executed by the hardware 80. According to the control program, a specific graphic user interface is generated on the screen having active icons of control keys, buttons, cursors and/or other manual control devices for controlling an imaging apparatus capable of only acquiring, processing, visualizing and saving B-mode images.

If, for example, the application relates to the determination of vascular flux, if this specific application is provided in the system, then a particular control program selection and activation button will be available which will charge in the hardware 80 a corresponding control program that relates to a corresponding virtual ultrasound apparatus having the functions of operating in the so called Doppler or Power Doppler-mode. Other functions which are not needed will be not present in the virtual ultrasound apparatus specialized for determining blood flux.

These are only two examples that can be of use to the skilled person in understanding the basic idea of the hardware/software structure of the present ultrasound system. Starting from this, the skilled person is able to construct any kind of specific application oriented machine and then the control program for generating the corresponding virtual machine.

Figure 22:
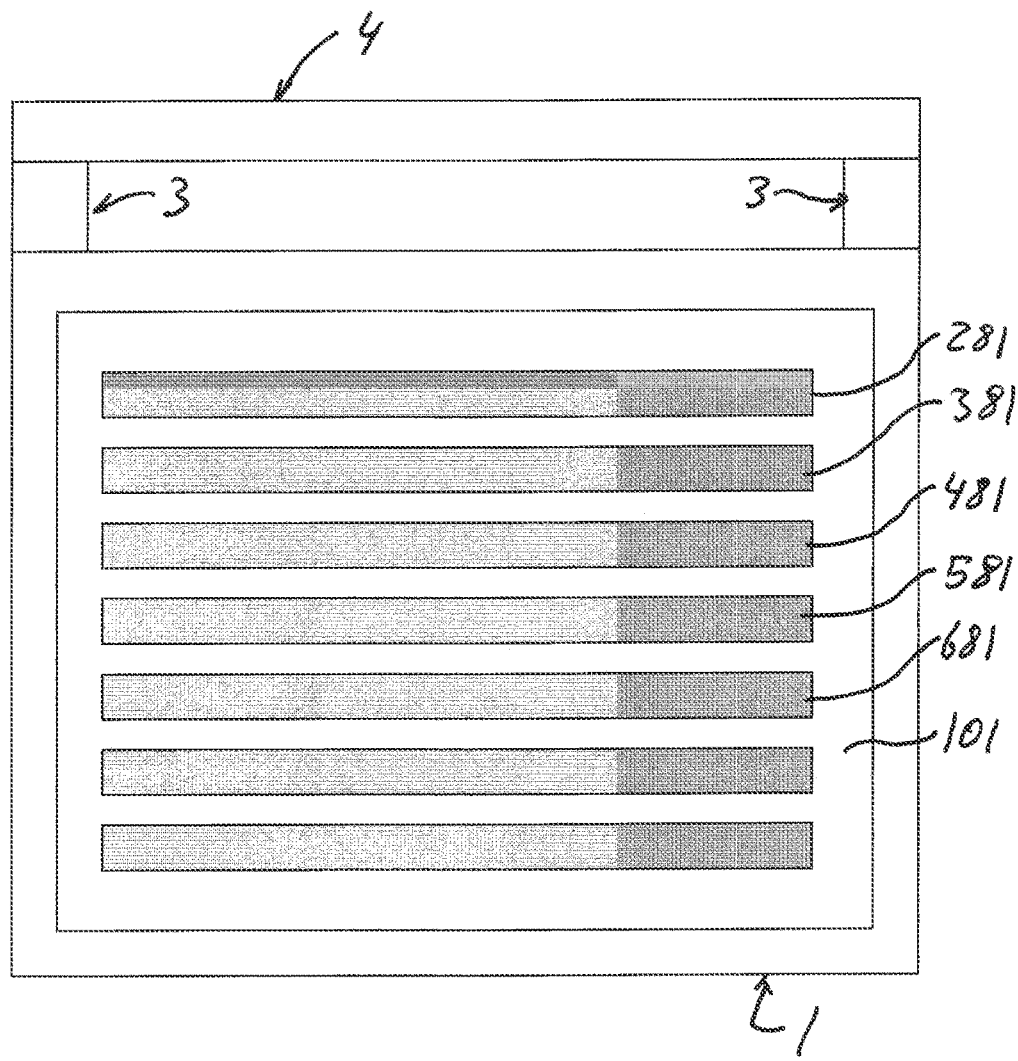
FIGS. 22 to 25 are examples of different GUI (graphic user Interface) for different applications to be carried out by the ultrasound system according to the present invention, which are generated by a software/hardware structure as disclosed in FIG. 18.

FIG. 22 illustrates diagrammatically the appearance of an example of the graphic user interface of a main control program.

Here, on the touch screen 82 a list of options appears, each of the options being associated to a selection and activation representation of a virtual key or button and each of the virtual key or button corresponding to an active area of the touch screen, which, when touched, will cause the main control program to address the specific application control program corresponding to the option selected and to load this control program in the operative memory of the hardware to execute this application specific control program.

In FIG. 22, seven selection and activation keys are shown as the graphic user interface of the main control program. Two of these correspond to the setup control programs which are indicated with 281 and 381 in FIG. 21 such as the power management setup and the hardware configuration setup. The other five keys are related to five different application specific configurations of an ultrasound system.

Figure 23:
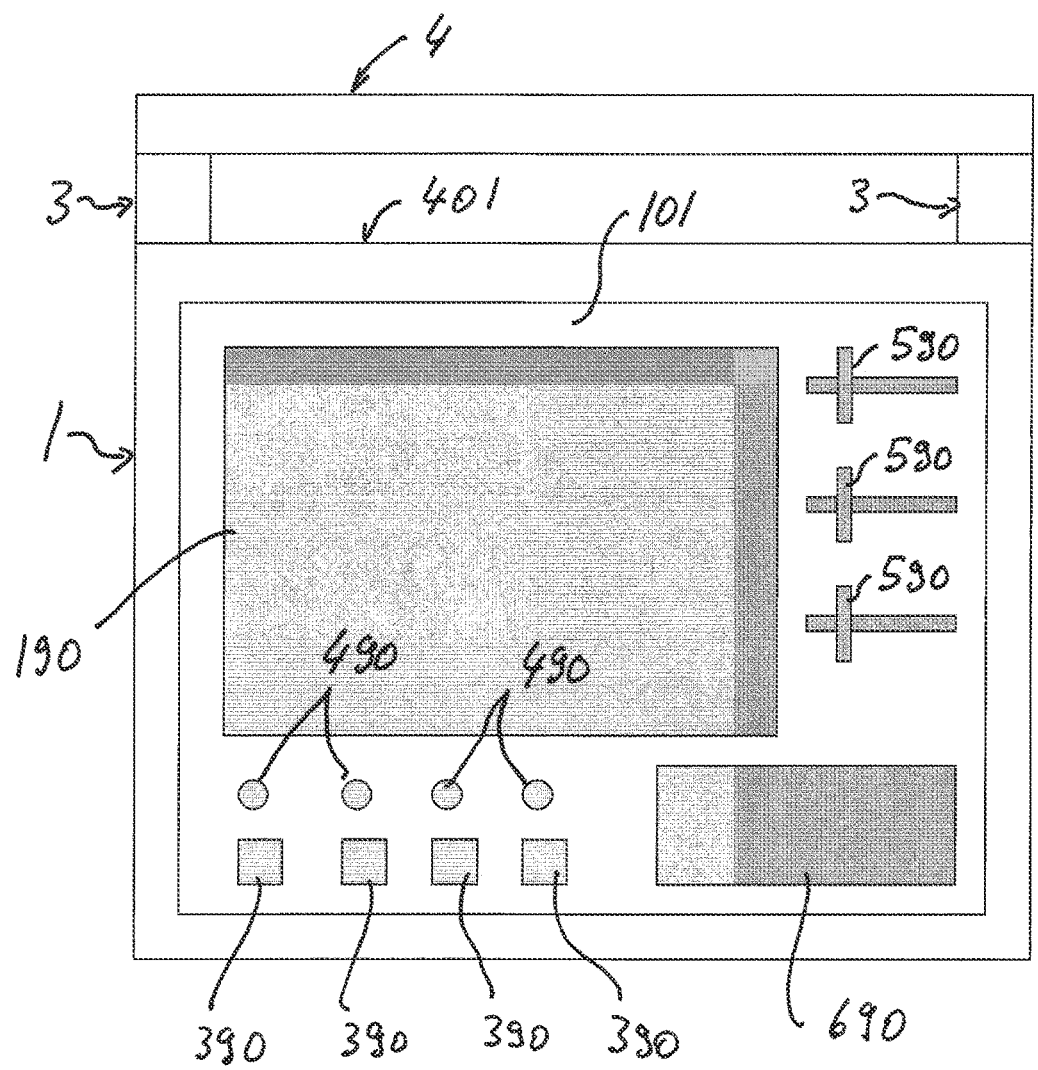
Figure 24:
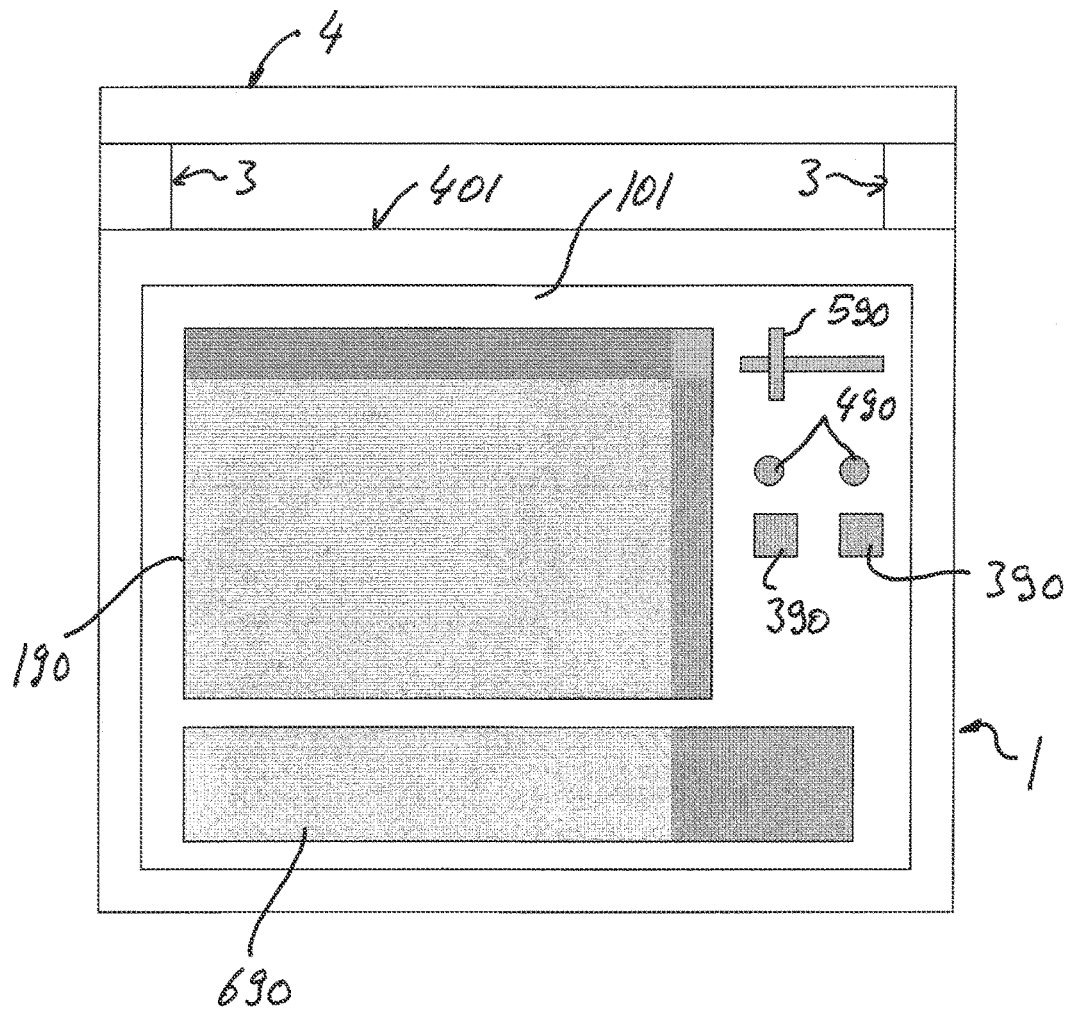
Figure 25:
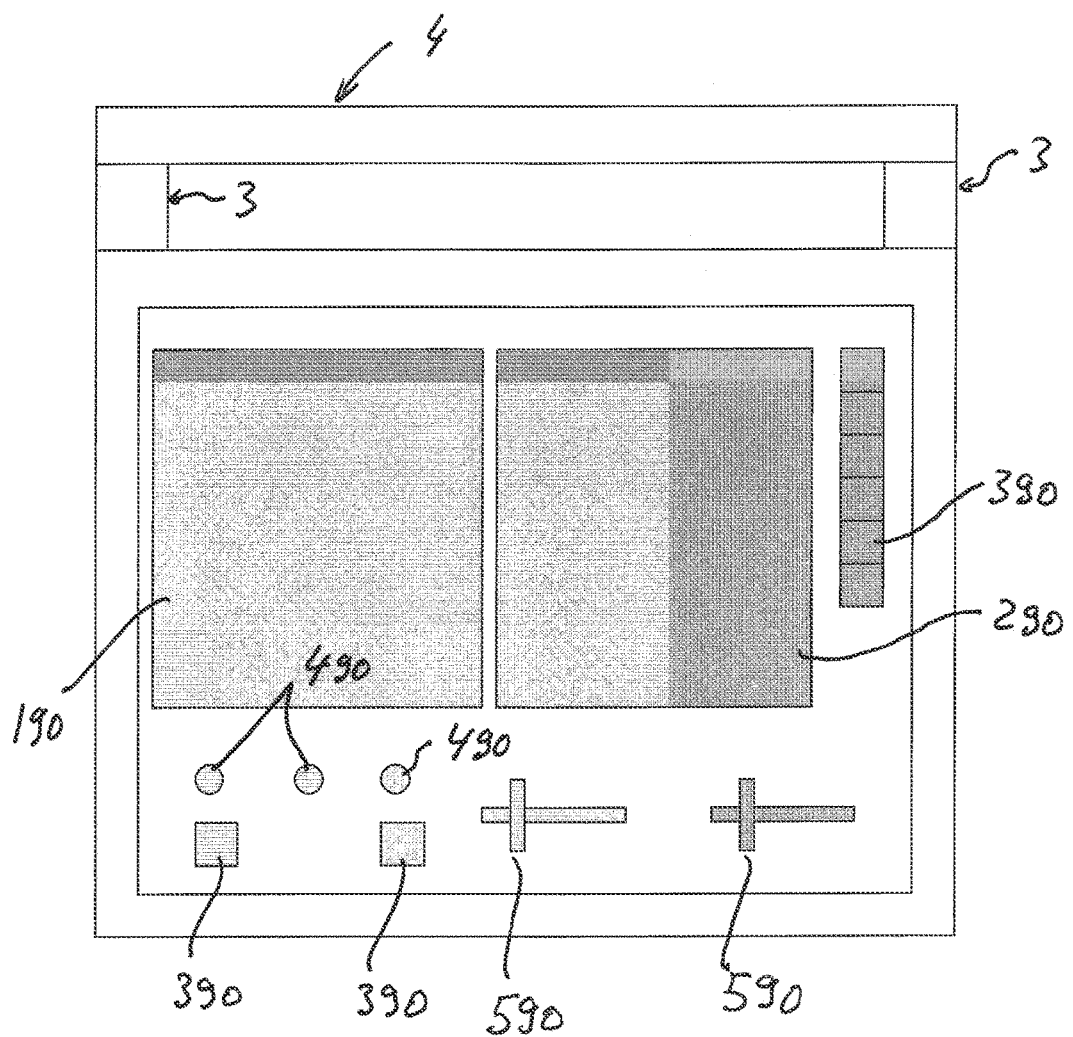

FIGS. 23 to 25 illustrate three different graphic user interfaces corresponding to three different virtual machines generated by three different application specific control programs such as, for example, the ones indicated with the numerals 481, 581 and 681 in FIG. 21.

As it appears clearly, the graphic user interface printed on the touch screen comprises different visualization areas of one or two images indicated by 190, 290; different numbers of keys indicated with the numerals 390 and different numbers of signal lights indicated by the numeral 490; different numbers of cursors indicated by the numeral 590. Furthermore, the keys 390, the lights 490 and the cursor 590 have different positions on the area of the touch screen as also the image visualization areas 190, 290. Additional areas 690 of the screen 90 can be provided for visualizing more information in the form of an alphanumeric text.

The advantages of the above described architecture are first of all that there is no mechanical control to be activated or driven by the user, so that there is no problem of long term damages to mechanical devices. Furthermore, a hardware configuration would require that a certain number of keys buttons, levers, or other control means that can be activated manually have to be present, which for a specific application would be superfluous. Using a graphic user interface the configuration of the manually driven control means can be changed every time in a way which is specific to the imaging application to be carried out, so that the configuration of the machine representing the ultrasound system can be limited every time to the provision of the very essential manual controls and thus to the very essential functions.

Beside saving in the dimensions of the touch screen, in the computational power and in the memory space and thus in the electric power consumption, every graphic user interface corresponding to a certain application specific configuration of the ultrasound system is very simple to use. It is also very simple to learn to use the application specific ultrasound system, since the keys, buttons, cursors and the other commands are limited to the ones needed for controlling the application specific machine that is being selected.

In loading the different control programs corresponding each to an application specific configured ultrasound apparatus, the generic hardware is controlled to carry out functions which in the currently known devices are carried out by dedicated hardware. Only very specific functions will need specific hardware, which will have its corresponding software to be correctly driven in combination with the functions carried out by the generic hardware controlled by the control program.

In regard to the above description, it has to be emphasized that only some examples are considered among a great number of possible choices.

A possible list of applications, for each one of which a specific virtual machine is provided in the form of a specific control program generating also a dedicated layout of controls that is optimized relative to the specific application, comprises the following applications:

Regional Anesthesia including Nerve Blocking and Vascular Access;

Veterinary including large and small animals;

Advanced Vascular including Blood Vessel Thickness and Stiffness;

Musculoskeletal including Wound View, Sports Medicine and Phlebology;

Esthetical surgery including Fat Thickness and Botox treatment.

The provision of an application specific layout of the control interfaces to the apparatus, which limits the controls to those that are really necessary for controlling the application specific tasks and functions, allows also generating very simple tutorials which are in the form of executable tutorial programs and which are each dedicated to a specific application. Particularly, each tutorial is a complete demo of the way of using the ultrasound system in an application specific configuration. Furthermore, because the application specific control programs do not need a huge amount of memory and computational power, each of the programs can also be provided with online help, which can print on the screen help messages either automatically or by a request command.

Coming to the detail of the hardware, the generic hardware can be of the kind of a processing unit such as a computer motherboard with an integrated video and audio chip, a communication bus with hard drives, a PCI bus for connecting several peripherals, USB and/or Parallel and/or serial and/or network communication hardware and ports, a solid state memory for loading the control programs to be executed, and a processor. The touch screen is connected to the video chip and has its own processor and a GPU (graphic processing unit). According to an additional feature of the present invention, in order to limit the size and expenses of the hardware and also the weight of the device without losing computational power, some routines of the control programs representing the virtual apparatuses, which are functional units consisting in software that drives the generic hardware to carry out the functions of the corresponding unit, are generated to be carried out by the GPU instead of the CPU (central processing unit). A particular example consists in providing a software scan-converter, which is the software version of the currently used hardware scan converter. This software scan-converter is executed by the GPU using zero CPU resources. Since the GPU has a considerable computational power, which is normally not completely exploited in this case, some computational work is passed from the CPU to the GPU so that the CPU is free to carry out other tasks.

While the invention has been described in connection with the above described embodiments, it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become obvious to those skilled in the art and the scope of the present invention is limited only by the appended claims.

The invention claimed is:

1. A portable ultrasound diagnostic system comprising:
a probe configured to transmit and receive an ultrasonic signal to and from a region of interest;
a main unit comprising circuitry in communication with said probe and configured to form an image of the region of interest based on the ultrasonic signal;
a display configured to display the formed image;
an anatomic saddle-shaped contact part which is configured to be fitted onto a forearm and which is attachable to the main unit by snap fasteners; and
a table base which is attachable to the main unit by snap fasteners;
wherein the main unit can be alternatively attached to the saddle-shaped contact part and to the table base, the said snap fasteners being the same for the saddle-shaped contact part and for the table base,
wherein the probe is connected to the circuitry in the main unit by a cable connection,
wherein the main unit has a weight supportable by one arm,
wherein the main unit has a case in the form of a tablet computer, having a front side formed by the display and a rear side, the main unit further having a handle configured to be grasped by a hand connected to a forearm,
wherein the handle is formed by an elongated member rigidly secured to the case of the main unit by arms cantilevered and protruding from the case in a direction of the rear side of the case of the main unit and terminating behind the rear side,
wherein the elongated member forming the handle comprises flat and parallel longitudinal surfaces and extends at a predetermined distance behind the rear side of the case of the main unit and is nearer to one of two opposite peripheral edges of the case of the main unit such that, when the hand grasps the handle, the case of the main unit leans against the forearm, an entire weight of the main unit being carried by the forearm, and
wherein the saddle-shaped contact part has a distance from the handle such that when the saddle-shaped contact part is secured to the forearm the hand can grasp the handle in such a way that fingers are free to move and operate on the handle.

2. The portable ultrasound diagnostic system according to claim 1, wherein the elongated member carries at least one or more control buttons or keys, which are connected to the circuitry of the main unit and generate and send commands to the main unit and activate or deactivate functions of the portable ultrasound system, said buttons or keys being actuatable by all the fingers of the hand.

3. The portable ultrasound diagnostic system according to claim 1, wherein the arms supporting the elongated member are telescopically adjustable in length.

4. The portable ultrasound diagnostic system according to claim 1, wherein the elongated member forming the handle is oriented parallel to a peripheral edge of the display.

5. The portable ultrasound diagnostic system according to claim 1, wherein the case of the main unit is configured to be carried either in a portrait or in landscape orientation of the display, and wherein the case has a rectangular parallelepiped shape, and wherein the elongated member is disposed in a direction parallel to a longer side of the case, in order to have a secure support of the case in both the portrait and landscape orientations, a length of the case in a direction parallel to a longitudinal axis of the elongated member being less than twice an average distance from a palm of the hand to a hollow of an elbow connected thereto.

6. The portable ultrasound diagnostic system according to claim 1, further comprising, in combination with the case of the main unit, an additional case having a front side secured to a back side of the case of the main unit, the additional case having a perimeter corresponding to a perimeter of the main case and housing one or more additional battery packs, hardware, a peripheral or a mass storage device, wherein the additional case is releasably connected mechanically and electrically with the main unit.

7. The portable ultrasound diagnostic system according to claim 1, further comprising at least one additional elongated member that is configured to be mechanically secured to an external surface of the elongated member forming the handle and that is shaped as an enclosure configured to stably house battery packs, such that the battery packs are extractable from and insertable in the additional elongated member for substitution with charged battery packs.

8. The portable ultrasound diagnostic system according to claim 1, wherein the elongated member forming the handle is releasably secured to the case of the main unit, two or more different elongated members being provided which are different in size from one another such to house a different number of battery packs;

further comprising releasable attachment devices of the elongated members having a same shape and dimensions for every different elongated member so that each of the elongated members is securable to the case of the main unit, wherein the releasable attachment devices are selected from the group consisting of snap fasteners, screw-connections, or combinations thereof.

9. The portable ultrasound diagnostic system according to claim 1, wherein the elongated member forming the handle is provided at a distance from a peripheral lateral edge of the case of the main unit on an opposite side of a second lateral peripheral edge of the case nearer to the elongated member, the distance corresponding to an average distance from a palm of the hand to a hollow of an elbow connected thereto, wherein the elongated member has a plurality of separated chambers each configured to house one or more battery packs, each chamber having an opening shaped for inserting and extracting a corresponding battery pack or battery packs and further having a removable member door closing the opening, each of the chambers being provided with contact terminals of a power feeding line which is connected to a power input of the main unit by conductors passing through one or both of the arms linking the elongated member to the case of the main unit, further comprising an attachment member provided for said case of the main unit, said attachment member being mountable around the forearm of a system user such that said display is visible to the system user during use, said attachment member being tightenable around the forearm for securing the case to the forearm without engaging the hand extending from the forearm, wherein the attachment member comprises at least one strap secured to the rear side of the case of the main unit, the strap having two ends which are configured to be secured to one another, and wherein the at least one strap is configured to be secured to the rear side of the case of the main unit such to make the case rotatable around an axis perpendicular to the rear side of the case of the main unit, and such that the main unit is rotatable to portrait and landscape orientations of the display when the strap is tightly secured to the forearm, and wherein the attachment member comprises a combination of said strap and an anatomic saddle-shaped contact part which is configured to be fitted onto the forearm, one or more additional battery packs being housed within the saddle-shaped contact part.

10. The portable ultrasound diagnostic system according to claim 9, wherein the distance of the elongated member from the lateral peripheral edge on the side of the case opposite to the second lateral peripheral edge is adjustable by securing the arms supporting the elongated member to one or more of the case of the main unit or ends of the elongated member in a swingable way.

11. The portable ultrasound diagnostic system according to claim 9, wherein the at least one strap is provided in an intermediate position between the elongated member and the side of the case of the main unit opposite to the side nearer to the elongated member.

12. The portable ultrasound diagnostic system according to claim 11, wherein the saddle-shaped contact part is rotatably securable to the rear side of the case of the main unit around an axis perpendicular to the rear side and wherein the saddle-shaped contact part is configured to be releasably stopped in one of at least two angular positions corresponding to portrait and landscape orientations of the display.

13. The portable ultrasound diagnostic system according to claim 12, further comprising one or more of additional battery packs or additional hardware housed in the saddle-shaped contact part.

14. The portable ultrasound diagnostic system according to claim 13, wherein the saddle-shaped contact part is releasably secured to the rear side of the case of the main unit, two or more saddle-shaped contact parts being provided which differ from one another in dimensions so to house one or more of a different number of battery packs or one or more different additional hardware units.

15. The portable ultrasound diagnostic system according to claim 1, wherein the elongated member is hollow and forms a case configured to house at least one or more of part of the circuitry of the main unit.

16. The portable ultrasound diagnostic system according to claim 15, wherein the elongated member has one or more chambers in which a power feeding circuit is housed, the power feeding circuit being connected to an external power network or source and having an output connected to a power feeding line of the main unit, the power feeding line being provided in the elongated member.

17. The portable ultrasound diagnostic system according to claim 16, further comprising a battery pack recharger which is fed by the power feeding circuit and which is connected to the battery packs in the elongated member by the power feeding line present in the elongated member or to a separate recharging line provided in the elongated member and branching in each of the chambers housing the battery packs, wherein the recharging line in the chambers has terminal contacts which are electrically connectable to recharging inputs of each of the battery packs.

18. The portable ultrasound diagnostic system according to claim 1, further comprising an additional electric power unit shaped as a docking unit or integrated in a docking unit, the docking unit having a case with front and back sides of a same form as the front and the rear sides of the case of the main unit, the case of the docking unit and the case of the main unit mechanically and releasably securable to one another and further releasably connecting together power and or communication lines provided in both the case of the main unit and the case of the docking unit.

19. The portable ultrasound diagnostic system according to claim 18, wherein the docking unit houses additional peripherals comprising one or more of special computing circuitry, storage devices, reading/writing devices of portable storage media, or modems, ports for connection of peripherals, hardware and ports for the connection to a network, or other devices.

20. The portable ultrasound diagnostic system according to claim 1,
wherein there is only a completely graphical user interface for inputting manual commands, further comprising a monitor screen configured as a touch screen that receives commands by touching the touch screen,
wherein the graphical user interface provides graphic symbols representing keys, buttons, switches, or cursors that provide commands to the portable ultrasound diagnostic system,
wherein at least one specific application is selectable within a list of application which are available on the portable ultrasound system,
wherein a specific graphic user interface program is loaded, which generates on the touch screen images of only one or more of the keys, buttons, switches, or cursors needed for carrying out tasks related to a selected specific application,
wherein a central processing unit executes different control programs and carries out different tasks, at least a memory being provided in which there are saved different programs for controlling the central processing unit for carrying out specific tasks related to functions of an echographic system, one or more of the different programs for carrying out the specific tasks being loaded and executed by the central processing unit when a specific application has been selected by a user,
wherein a main control program is loaded and executed by the central processing unit and prints on a display screen a list of applications available with the portable ultrasound system, a graphic user interface comprising icons of keys, buttons, switches, or cursors, and
wherein the main control program addresses, depending on a choice made with menus, programs for carrying out the specific tasks related to the applications, configuration, or adjustment options chosen by the user.

21. The portable ultrasound diagnostic system according to claim 20, further comprising a control program saved in the memory and available for being executed by the central processing unit, the control program comprising an application specific tutorial program for the user that is available in a ready to start condition of the portable ultrasound system,
wherein the control program prints on the screen a graphic user interface with a key icon which addresses the tutorial program and which, when touched by the user, causes the control program to load the tutorial program and the central processing unit to execute the tutorial program.

22. The portable ultrasound diagnostic system according to claim 21, wherein, in order to spare electric power and maintain a limited weight without affecting computational power of the system needed by hardware for executing programs and carrying out tasks of the system, a part of the tasks to be carried out by the central processing unit (CPU) are carried out by a graphic processing unit (GPU).

23. A portable ultrasound diagnostic system comprising:
a probe configured to transmit and receive an ultrasonic signal to and from a region of interest;
a main unit comprising circuitry in communication with said probe and configured to form an image of the region of interest based on the ultrasonic signal;
a display configured to display the formed image;
an anatomic saddle-shaped contact part which is configured to be fitted onto a forearm and which is attachable to the main unit by snap fasteners; and
a table base which is attachable to the main unit by snap fasteners;
wherein the main unit can be alternatively attached to the saddle-shaped contact part and to the table base, the said snap fasteners being the same for the saddle-shaped contact part and for the table base,
wherein the probe is connected to the circuitry in the main unit by a cable connection,
wherein the main unit has a weight supportable by one arm,
wherein the main unit has a case in the form of a tablet computer, having a front side formed by the display and a rear side, the main unit further having a handle configured to be grasped by a hand connected to the forearm,
wherein the handle is formed by an elongated member rigidly secured to the case of the main unit by arms cantilevered and protruding from the case in a direction of the rear side of the case of the main unit and terminating behind the rear side,
wherein the elongated member forming the handle comprises flat and parallel longitudinal surfaces and extends at a predetermined distance behind the rear side of the case of the main unit and is nearer to one of two opposite peripheral edges of the case of the main unit such that, when the hand grasps the handle, the case of the main unit leans against the forearm connected to the hand, an entire weight of the main unit being carried by the forearm,
wherein the saddle-shaped contact part has a distance from the handle such that when the saddle-shaped contact part is secured to the forearm the hand can grasp the handle in such a way that fingers are free to move and operate on the handle,
wherein the elongated member forming the handle is provided at a distance from a peripheral lateral edge of the case of the main unit on an opposite side of a second lateral peripheral edge of the case nearer to the elongated member, the distance corresponding to an average distance from a palm of the hand to a hollow of an elbow connected thereto, wherein the elongated member has a plurality of separated chambers each configured to house one or more battery packs, each chamber having an opening shaped for inserting and extracting a corresponding battery pack or battery packs and further having a removable member door closing the opening, each of the chambers being provided with contact terminals of a power feeding line which is connected to a power input of the main unit by conductors passing through one or both of the arms linking the elongated member to the case of the main unit, further comprising an attachment member provided for said case of the main unit, said attachment member being mountable around the forearm of a system user such that said display is visible to the system user during use, said attachment member being tightenable around the forearm for securing the case to the forearm without engaging the hand extending from the forearm, wherein the attachment member comprises at least one strap secured to the rear side of the case of the main unit, the strap having two ends which are configured to be secured to one another, and wherein the at least one strap is configured to be secured to the rear side of the case of the main unit such to make the case rotatable around an axis perpendicular to the rear side of the case of the main unit, and such that the main unit is rotatable to portrait and landscape orientations of the display when the strap is tightly secured to the forearm, and wherein the attachment member comprises a combination of said strap and an anatomic saddle-shaped contact part which is configured to be fitted onto the forearm, one or more additional battery packs being housed within the saddle-shaped contact part, wherein the at least one strap is provided in an intermediate position between the elongated member and the side of the case of the main unit opposite to the side nearer to the elongated member, and wherein the saddle-shaped contact part is rotatably securable to the rear side of the case of the main unit around an axis perpendicular to the rear side and wherein the saddle-shaped contact part is configured to be releasably stopped in one of at least two angular positions corresponding to portrait and landscape orientations of the display, further comprising one or more of additional battery packs or additional hardware housed in the saddle-shaped contact part, wherein the saddle-shaped contact part is constructed as a unit formed by a plurality of parts mounted one to another, the plurality of parts comprising a second case securable in an intermediate position between the saddle-shaped contact part and the rear side of the case of the main unit, the second case having one side connectable to the rear side of the case of the main unit using a same connector as on the saddle-shaped contact part, the second case being connected to the saddle-shaped contact part using same connection devices as on the rear side of the case of the main unit.

24. The portable ultrasound diagnostic system according to claim 23, wherein more than one additional case is provided, each of the additional cases being securable to another additional case and in an intermediate position between the saddle-shaped contact part and the rear side of the case of the main unit.

\* \* \* \* \*